US005646248A

United States Patent [19]

Sawada et al.

[11] Patent Number: 5,646,248

[45] Date of Patent: Jul. 8, 1997

[54] E-SELECTION BINDING SOLUBLE LAMP-1 POLYPEPTIDE

[75] Inventors: Ritsuko Sawada, San Diego, Calif.; John B. Lowe, Ann Arbor, Mich.; Minoru Fukuda, San Diego, Calif.

[73] Assignee: La Jolla Cancer Research Foundation, La Jolla, Calif.

[21] Appl. No.: 73,807

[22] Filed: Jun. 8, 1993

[51] Int. Cl.[6] .......................... C07K 14/435; C12N 15/12

[52] U.S. Cl. .......................... 530/350; 435/69.1; 536/235

[58] Field of Search .................................... 530/350, 395; 435/69.1; 536/23.5; 514/12

[56] References Cited

PUBLICATIONS

Sueyoshi et al., J. Biol. Chem., vol. 269, pp. 32342–32350, 1994.

Carlsson, Sven R. and Fukuda, Minoru. "The Lysosomal Membrane Glycoprotein Lamp–1 is Transported to Lysosomes by Two Alternative Pathways." Archives of Biochem. and Biophysics. 296:630–639 (1992).

Sawada, R, Tsuko et al., "The Genes of Major Lysosomal Membrane Glycoproteins, Lamp–1 and Lamp–2." J. Biol. Chem. 268:9014–9022 (1993).

Fukuda, Minoru et al., "Cloning of cDNAs Encoding Human Lysosomal Membrane Glycoproteins, H–Lamp–1 and h–lamp–2." J. Biol. Chem. 263:18920–18298 (1988).

Carlsson, Sven R. et al., "Isolation and Characterization of Human Lysosomal Membrane Glycoproteins, h–lamp–1 and h–lamp–2." J. Biol. Chem. 263:18911–18919 (1988).

Lasky, Laurence A. et al., "An Endothelial Ligand for L–Selection Is A Novel Mucin–like Molecule." Cell. 69:927–938 (1992).

Lowe, John B. et al., "ELAM–1–Dependent Cell Adhesion to Vascular Endothelium Determined by a Transfected Human Fucosyltranzferase cDNA." Cell. 63:475–484 (1990).

Mane, Shrikant M. et al., "Purification of Characterization of Human Lysosmal Membrand Glycoproteins." Archives of Biochemistry and Biophysics. 268:360–378 (1989).

Harter, Cordula and Mellman, Ira "Transport of the Lysosomal Membrane Glycoprotein lgp120 (lgp–A) to Lysosomes Does Not Require Appearance on the Plasma Membrane." J. Cell Biology 117:311–325 (1992).

Saitoh, Osamu et al., "Diffential Glycosylation and Cell Surface Expression of Lysosomal Membrane Glycoproteins in Sublines of a Human Colon Cancer Exhibiting Distincy Metastatic Potentials." J. Biol. Chem. 267:5700–5711 (1992).

Lee, Ni et al., "Granulocytic Differentiation of HL–60 Cells is Associated with Increase of Poly–N–acetyllactosamine in Asn–linked Oligosacchrides Attached to Human Lysosomal Membrane Glycoproteins." J. Biol. Chem. 265:20476–20487 (1990).

Springer, Timothy A. "Adhesion Receptors of the Immune System." Nature. 346:425–434 (1990).

Kuijpers, Taco W. et al., "CD66 Nonspecific Cross–reacting Antigens Are Involved in Neutrophil Adherence to Cytokine–activitated Endothelial Cells." J. Cell. Biol. 118:457–466 (1992).

Lawrence, Michael B. et al., "Leukocytes Roll on a Selectin at Physiologic Flow Rates: Distinction from and Prerequisite for Adhesion through Integrins." Cell 65:859–873 (1991).

Polley, Margaret J. et al., "CD62 and Endothelial cell–leukocyte Adhesion Molecule 1 (ELAM–1) Recognize the Same Carbohydrate Ligand, Sialyl–Lewis x." Proc. Natl. Acad. Sci. USA. 88:6224–6228 (1991).

Viitala, Juha et al., "Molecular Cloning of cDNAs Encoding Lamp A, a human Lysosomal Membrane Glycoprotein with Apparent $M_r \approx 120,000$." Proc. Natl. Acad. Sci. USA 85:3743–3747 (1988).

Yamashita, Katsuko et al., "Carbohydrate Structures of Nonspecific Cross–reacting Antigen–2, a Clycoprotein Purified from Meconium as an Antigen Cross–reacting with Anticarcinoembryonic Antigen Antibody." J. Biol. Chem. 264:17873–17881 (1989).

Mulligan, Michael S. et al., "Role of Endothelial–Leukocyte Adhesion Molecule 1 (ELAM–1) in Neutrophil–mediated Lung Injury in Rats." J. Clin. Invest. 88:1396–1406 (1991).

Ley, Klaus et al., "Lectin–Like Cell Adhesion Molecule 1 Mediates Leukocyte Rolling in Mesenteric Venules in Vivo." Blood 77:2553–2555 (1991).

Lippincott–Schwartz, Jennifer et al., "Cycling of the Integral Membrane Glycoprotein LEP100, between Plasma Membrane and Lysosomes: Kinetic an Morphological Analysis." Cell 49:669–677 (1987.

Williams, Mark A. and Fukuda, Minoru, "Accumulation of Membrane Glycoproteins in Lysosomes Requires a Tyrosine Residue at a Particular Position in the Cytoplasmic Tail." J. Cell Biology. 111:955–966 (1990).

Kim, Young S. et al., "$Le^x$ and $Le^y$ Antigen Expression in Human Pancreatic Cancer." Cancer Res. 48:475–482 (1988).

Carlsson, Sven R. and Fukuda, Minoru. "Structure of Human Lysosomal Membrane Glycoprotein 1." J. Biol. Chem. 264:20526–20531 (1989).

Fukuda, Michiko N. et al., "Structures of Glycosphingolipids Isolated from Human Granulocytes." J. Biol. Chem. 260:1067–1082 (1985).

Mathews, Paul M. et al., "The Pathway and Targeting Signal for Delivery of the Integral Membrane Glycoprotein LEP100 to Lysosomes." J. Cell Biology. 118:1027–1040 (1992).

(List continued on next page.)

*Primary Examiner*—Stephen G. Walsh
*Assistant Examiner*—Sally P. Teng
*Attorney, Agent, or Firm*—Campbell & Flores LLP

[57] ABSTRACT

The present invention provides novel purified human lysosomal membrane sialoglycoproteins. These novel human proteins, lamp-1 and lamp-2, are highly glycosylated and are the major carriers of polylactosaminoglycan, when expressed on the cell surface participate in various cellular adhesion interactions.

6 Claims, 6 Drawing Sheets

OTHER PUBLICATIONS

Mizoguchi, Akira et al., "Changes in Asparagine–linked Sugar Chains of Human Promyelocytic Leukemic Cells (HL–60) during Monocytoid Differentiation and Myeloid Differentiation." J. Biol. Chem. 259:11949–11957 (1984).

Maemura, Kentaro and Fukuda, Minoru "Poly–N–acetyllactosaminyl o–Glycans Attached to Leukosialin." J. Biol. Chem. 267:24379–24386 (1992).

Fukushima, Kiyoyasu et al., "Characterization of Sialosylated Lewis$^x$ as a New Tumor–associated Antigen." Cancer Res. 44:5279–5285 (1984).

Kameyama, Akihiko et al., "Total Synthesis of Sialyl Lewis X*." Carbohy. Res. 209:C1–C4 (1991).

Laferte, Suzanne and Dennis, James W. "Purification of Two Glycoproteins Expressing β1–6 Branched Asn–Linked Oligosaccharides from Metastatic Tumour Cells." Biochem J. 259:569–576 (1989).

Moore, Kevin L. et al., "Identification of Specific Glycoprotein Ligand for P–selection (CD62) on Myeloid Cells." J. Cell Biol. 118:445–456 (1992).

Phillips, M. Laurie, et al., "ELAM–1 Mediates Cell Adhesion by Recognition of a Carbohydrate Ligand. Sialyl–Le$^x$." Science. 250:1130–1131 (1990).

Walz, Gerd, et al., "Recognitiion by ELAM–1 of the Sialyl–Le$^x$ Determinant of Myeloid and Tumor Cells." Science. 250:1132–1135 (1990).

Picker, Louis J. et al., "The Neutrophil Selection LECAM–1 Presents Carbohydrates Ligands to the Vascular Selectins ELAM–1 and GMP–140." Cell 66:921–933 (1991).

Larsen, Eric et al., "PADGEM–Dependent Adhesion of Platelets to Monocytes and Neutrophils is Mediated by a Lineage–Specific Carbohydrate, LNF III (CD15)." Cell 63:467–474 (1990).

Magnani, John L. et al., "A Monoclonal Antibody–defined Anitgen Associated with Gastrointestinal Cancer is a Ganglioside Containing Siaylylated Lacto–N–fucopentaose II." J. Biol. Chem. 257:14365–14369 (1992).

Holmes, Eric H. et al., "Biosynthesis of the Sialyl–Le$^x$ Determinant Carried by Type 2 Chain Glycosphingolipids ($IV^3NeuAcIII^3FucnLc_4$, $VI^3NeuAcV^3FucnLc^6$, and $VI^3NeuAcIII^3V^3Fuc_2Lc_6$) in Human Lung Carcinoma PC9 Cells." J. Biol. Chem. 261:3737–3743 (1986).

Berg, Ellen L. et al., "A Carbohydrate Domain Common to Both Sialyl Le$^a$ and Sialyl Le$^x$ is Recognized by the Endothelial Cell Leukocyte Adhesion Molecule ELAM–1." J. Biol. Chem. 266:14869–14872 (1991).

E-SELECTION BINDING SOLUBLE LAMP-1 POLYPEPTIDE

This invention was made in part with Government support under Grant Nos. R01 CA48737 and P01 AI33189 from the National Institutes of Health. The Government may have certain rights in this invention.

BACKGROUND OF THE INVENTION

Adhesive interactions of cells with other cells and with the extracellular matrix are crucial to all developmental processes, but have a central role in the functions of the immune system throughout life. Leukocyte trafficking, recruitment to sites of inflammation, tumor cell adhesion to endothelial cells and metastasis are mediated by three adhesion receptor families, the integrin and immunoglobulin superfamilies and the recently described selectin family. The known selectins contain an N-terminal lectin domain that mediates adhesion by binding carbohydrate ligands on opposing cells. The lectin domain is followed by an epidermal growth factor-like domain and a series of consensus repeats similar to those found in complement regulatory proteins. The selectins are expressed on activated endothelial cells and platelets and are implicated in the recruitment of neutrophils and monocytes to sites of tissue injury.

E-selectin is a selectin that is transiently expressed on endothelial cells 2–8 hr after stimulation of IL-1 and other inflammatory agents, and mediates a neutrophil adhesion pathway distinct from that mediated by ICAMS and leukocyte integrins. The neutrophil chemoattractant IL-8, which is secreted by activated endothelial cells, acts on neutrophils as a feedback inhibitor to attenuate the hyperadhesive interaction between neutrophils and E-selectin receptors. P-selectin is located in α-granules of platelets and Weibel-Palade bodies of endothelial cells, and is rapidly mobilized to the surface of these cells after stimulation by products of the clotting cascade such as thrombin, where it mediates adhesion of neutrophils and monocytes. Selectins function in a wide range of cell interactions in the vasculature and are expressed both on leukocytes and endothelial cells. Selectins mediate adhesion events within the blood vascular compartment through calcium-dependent recognition of specific carbohydrates.

The acquisition of invasive properties by tumorigenic cells constitutes an essential step in tumor progression. Since most malignant tumors are carcinomas, the molecular mechanisms underlying the invasion of epithelial cells are of particular interest.

Over 90% of human tumors are carcinomas; in these, transformed epithelial cells grow in an uncontrolled fashion, break through the basement membrane, and invade the underlying mesenchyme. Local invasion can compromise the function of involved tissues. It has been shown that the state of differentiation and the concomitant degree of invasiveness of carcinomas can determine cancer progression. However, the most significant turning point in the disease is the establishment of metastasis. It is known that the malignant phenotype is the culmination of a series of genetic changes that involves both positive and negative regulatory elements. Investigation of the activation, regulation, mutation, or somatic deletion of genes that encode these regulatory elements presents a new frontier for research into the complex cellular interactions that precede the development of metastasis.

The morphological and functional characteristics of carcinomas were recognized years ago; the underlying molecular basis, however, is only presently accessible to the investigation on a molecular level. Thus, there is a great clinical need to elucidate the underlying molecular basis of cellular adhesion and its role in inflammatory responses and metastasis and to develop compounds that can modify these cellular interactions. The present invention satisfies this need and provides related advantages as well.

SUMMARY OF THE INVENTION

The present invention provides novel purified human lysosomal membrane sialoglycoproteins. These novel human proteins, lamp-1 and lamp-2, are highly glycosylated and are the major carriers of polylactosaminoglycan. Lamp-1 and lamp-2 proteins are expressed on the cell surface participate in various cellular adhesion interactions.

Further provided by the present invention are methods of modifying biological functions mediated by the regulatory activity of selectin receptors, methods of alleviating pathologic conditions mediated by lamp-derived polypeptide and selectin receptor interactions. Isolated nucleic acids encoding the novel lamp-1 and lamp-2 glycoproteins and soluble lamp-derived polypeptides are provided, as well as vectors containing the nucleic acids and recombinant host cells transformed with such vectors. This invention provides antisense oligonucleotides capable of binding specifically to mRNA molecules encoding human lamp-derived polypeptides. The present invention provides monoclonal antibodies to the soluble lamp-derived polypeptides. Methods of detecting the presence of activated selectin receptors on platelets and endothelial cell surfaces are also provided.

BRIEF DESCRIPTION OF THE DRAWINGS

FIG. 1A, SP cell transfectant obtained with pSVlamp-1. FIG. 1B, SP cell transfectant obtained with pSRαlamp-1. FIG. 1C, SP cell transfectant obtained with pSVlamp-$1^H$. FIG. 1D, SP cell transfectant obtained with pSRαlamp-$1^H$.

FIG. 4A is the protein staining while FIG. 4B is the Western blot by anti-lamp-1 antibodies.

DETAILED DESCRIPTION OF THE INVENTION

Figure 1A:
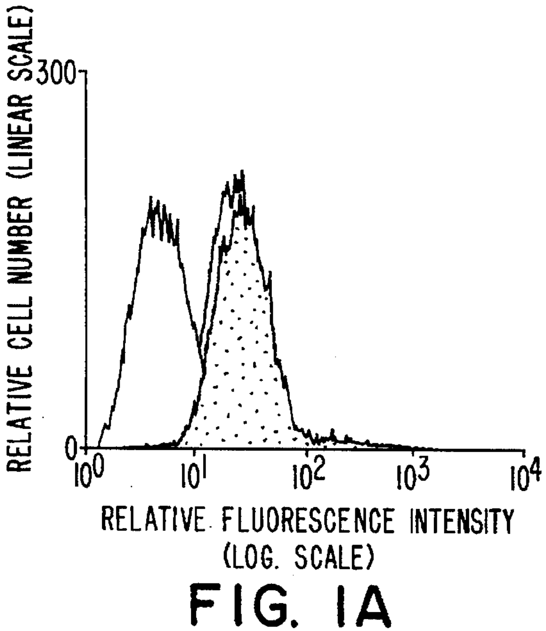
FIGS. 1A through 1D shows the results of flow cytometry analysis of cell surface lamp-1 on various SP cell lines. From the left, the solid lines represent profiles obtained by staining SP cell transfectants without primary anti-human lamp-1 antibody. Dotted lines represent profiles obtained by staining control, non-transfected SP cells with anti-human lamp-1. The filled profiles were obtained when SP cell transfectants were stained with anti-human lamp-1 antibody.
Figure 1B:
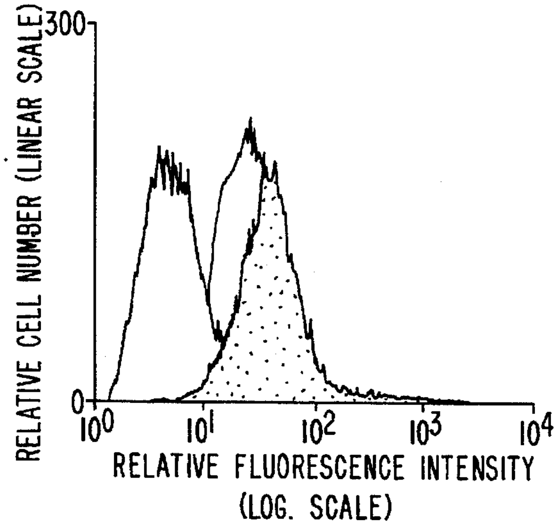
Figure 1C:
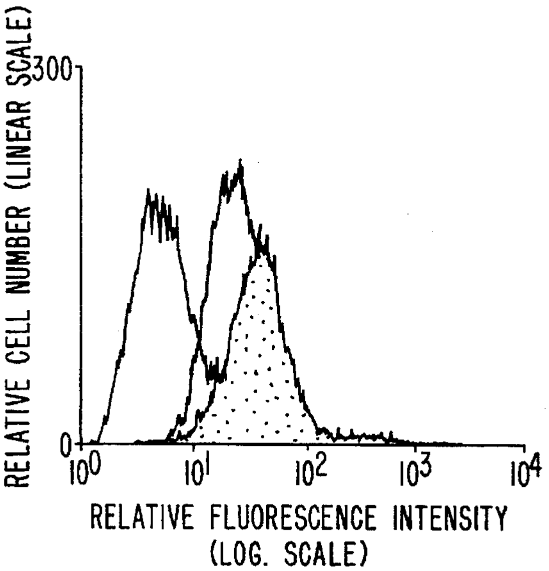
Figure 1D:
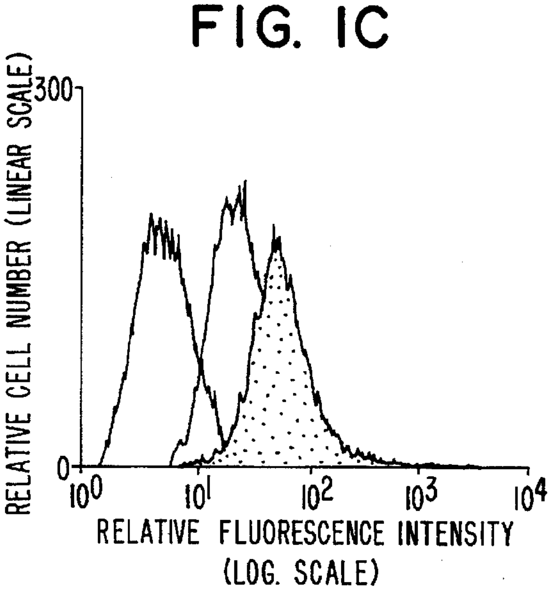

Lamp-1 and lamp-2 are the most abundant glycoproteins within the lysosomal membrane. Although the majority of lamp-1 and lamp-2 molecules reside in lysosomes, some lamp-1 and lamp-2 are expressed on cell surfaces (Lippincott-Schwartz et al., *Cell* 49:669–677 (1987); Mane et al., *Arch. Biochem. Biophys.* 268:360–378 (1989); Carlsson et al., *Arch. Biochem. Biophys.* 296:630–639 (1992) which are incorporated herein by reference), suggesting that those proteins can provide ligands for selectins. It has been shown that highly metastatic colonic carcinoma L4 cells express more lamp-1 and lamp-2 on the cell surface than low metastatic SP cells (Saitoh et al., *J. Biol. Chem.* 267:5700–5711 (1992) incorporated herein by reference).

The lysosomal membrane glycoproteins, lamp-1 and lamp-2, are the major carriers of polylactosaminoglycans in various cells (Viitala et al., *Proc. Natl. Acad. Sci. USA* 85:3743–3747 (1988); Carlsson et al., *J. Biol. Chem.* 263:18911–18919 (1988) both incorporated herein by reference), and as such are the major carriers for poly-N-acetyllactosamines that are able to display sialyl $Le^x$ termini. It has also been shown that lamp-1 is the major glycoprotein containing GlcNAcβ1→6 Manα1→6Man branching in metastatic tumor cells as detected by leukophytohemagglutin binding (Laferté et al., *Biochem. J.* 259:569–576 (1989) incorporated herein by reference).

Polylactosaminoglycans are high molecular weight carbohydrates and are distinguished from usual complex-type Asn-linked saccharides by having side chains composed of endo-β-galactosidase susceptible $(Gal\beta1\rightarrow4GlcNAc\beta1\rightarrow3)_n$ repeats. The structures of polylactosaminoglycans are often characteristic to different cell types and stages of differentiation. For example, the termini of human granulocyte and monocyte polylactosaminoglycans are enriched in the sialyl $Le^x$ moiety (NeuNAcα2→3Galβ1→4 (Fucα1→3) GlcNAc→R) while erythrocyte polylactosaminoglycans termini are enriched in Fucα1→2Galβ→4GlcNAc→R moieties, representing portions of the ABO blood group antigen. It was discovered recently that the terminal structures of poly-N-acetyllactosamines unique to granulocytes and monocytes serve as ligands for selectins present on endothelial cells and platelets. It has also been demonstrated that the isomer of sialyl $Le^x$, sialyl $Le^a$ NeuNAcα-2→3Galβ1→3 (Fucα1→4) GlcNAc→R also serves as a ligand for E-selectin. Reports from several laboratories have shown that the level of sialyl $Le^x$ or sialyl $Le^a$ is increased in tumor cells, particularly in carcinoma cells. It has also been demonstrated that some tumor cells adhere to endothelial cells by selectin-mediated interactions. These results suggest that tumor cells may adhere to endothelial cells at metastatic sites by the binding of E- or P-selectin to tumor cell surface carbohydrates.

In fact, it has been shown that highly metastatic colonic carcinoma cell lines express more lamp-1 and lamp-2 on the cell surface than poorly metastatic ones derived from a single human colon carcinoma (Saitoh et al., supra). It was also shown that the highly metastatic cell lines contain more poly-N-acetyllactosamine in carbohydrates attached to lamp molecules. These results suggest that tumor cells can modulate cell surface display of selectin ligands by regulating levels of cell surface lamp-1 and lamp-2 expression, and further suggest that upregulation of surface-localized lamp-1 and lamp-2 expression can therefore promote or facilitate the metastatic process.

The present invention demonstrates that increased expression of lamp-1 at the surface of colonic carcinoma cells leads to stronger adhesion to E-selectin expressing cells. Increased surface expression of lamp-1 was achieved by over-expression of lamp-1 or by expression of mutated lamp-1 that became a plasma membrane glycoprotein. Since low metastatic SP cells express only a small amount of lamp-1 on the cell surface, SP cells were chosen for increased expression of lamp-1 at the cell surface by gene transfer.

Figure 6:
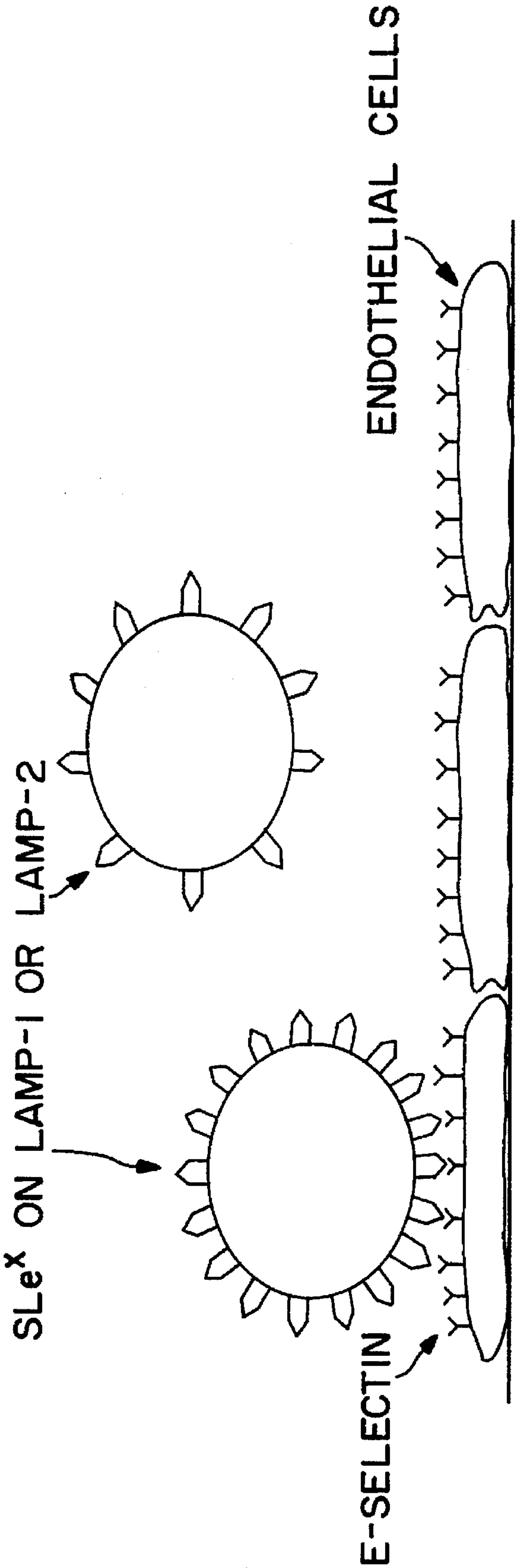
FIG. 6 shows the increase of lamp-1 molecules on the cell surface of SP colonic carcinoma cells results in increased adhesion to E-selectin-expressing cells. Low metastatic colonic carcinoma SP cells express a small amount of sialyl $Le^x$ on cell surface lamp molecules (see the right cell). When the same cells were transfected with lamp-1 expression vectors, the number of the cell surface lamp-1 molecules was increased. This increase was accompanied by an increased amount of cell surface sialyl $Le^x$ determinants and the increased efficiency of adhesion to E-selectin-expressing cells (see the left cell).

The results obtained in the Examples presented infra are consistent with the fact that lamp molecules are the major carriers of poly-N-acetyllactosamines in nucleated cells. As shown previously (Mizoguchi et al., *J. Biol. Chem.* 259:11949–11957 (1984); Fukuda et al., *J. Biol. Chem.* 260:1067–1082 (1985); Holmes et al., *J. Biol. Chem.* 261:3737–3943 (1986) which are incorporated herein by reference), poly-N-acetyllactosamines appeared to be preferred substrates for α1→3 fucosyltransferase and α2→3 sialyltransferase, thus efficiently providing sialyl $Le^x$ termini. Since SP colonic cells apparently contain these glycosyltransferases, the amount of cell surface sialyl $Le^x$ is almost certainly directly related to the amount of sialyl $Le^x$ on the cell surface lamp-1 (see FIG. 6).

The present results are clearly consistent with the notion that sialyl $Le^x$ structures present in lamp-1 serve well as ligands for E-selectin on the cell surface. In a corroborative experiment, the present study also demonstrated that a soluble lamp-1 can inhibit E-selectin mediated adhesion and such inhibition can be obtained only when the soluble lamp-1 was prepared from cells expressing sialyl $Le^x$ structures. The results demonstrate that lamp-1 can be an efficient inhibitor for E-selectin-mediated adhesion.

It was shown that sialyl $Le^x$ terminal structures can be present in glycolipids as well (Fukushima et al., *Cancer Res.* 44:5279–5285 (1984) incorporated herein by reference). Such glycolipids are particularly enriched in colonic carcinoma cells and it is plausible to assume that SP cells also contain such glycolipids. In the present study, the increased amount of lamp-1 significantly increased the adhesion of SP cells to endothelial cells and such adhesion can be inhibited efficiently by soluble lamp1- that contains sialyl $Le^x$ structures. These results suggest that sialyl $Le^x$ structures present on glycoproteins may be better ligands than those on glycolipids. It is possible that glycans attached to proteins may extend more, enabling selectin molecules to bind to the presented ligand (see Moore et al., *J. Cell Biol.* 118:445–456 (1992) incorporated herein by reference).

It was recently shown that the nonspecific cross-reacting antigen CD66 can inhibit E-selectin mediated adhesion (Kuijpers et al., *J. Cell Biol.* 118:457–466 (1992) incorporated herein by reference). CD66 is a member of the immunoglobulin superfamily and was shown to contain sialyl $Le^x$ termini when it was purified from meconium (Yamashita et al., *J. Biol. Chem.* 264:17873–17881 (1989) incorporated herein by reference). Although it is not clear if CD66 is the major presenter of sialyl $Le^x$ on neutrophils, the results are consistent with the present results, showing that a sialyl $Le^x$-containing glycoprotein can inhibit E-selectin mediated adhesion. On the other hand, it was reported recently that P-selectin binds preferentially to a glycoprotein with Mr.~120,000 (Moore, Supra). This molecule is different from lamp molecules or leukosialin, although both lamp (Saitoh et al., supra) and leukosialin (Maemura et al., *J. Biol. Chem.* 267:24379–24386 (1992) incorporated herein by reference) were found to contain sialyl $Le^x$ structures. It was shown that L-selectin on neutrophils may present sialyl $Le^x$ to E-selectin (Picker et al., *Cell* 66:921–933 (1991) incorporated herein by reference). On the other hand, L-selectin was found to preferentially bind to two glycoproteins on endothelial cells. Most recently a report demonstrated that one of those glycoproteins is a leukosialin-like glycoprotein containing a multiple number of O-glycans (Lasky et al., *Cell* 69:927–938 (1992) incorporated herein by reference). It is thus likely that glycans presented on this glycoprotein, termed Glycam, provide a better ligand(s) for L-selectin. It thus seems reasonable to assume that selectin ligands are preferentially presented to selectins by a limited number of glycoproteins. Nevertheless, the present study strongly suggests that lamp-1 may function to present sialyl $Le^x$ and also sialyl $Le^a$ on tumor cells, and most likely also on other cell types. Furthermore, our present study demonstrated that lamp-1 can be used as an efficient inhibitor in E-selectin mediated adhesion.

These results also strongly suggest that tumor cells utilize selectin-carbohydrate interaction when tumor cells adhere at metastatic sites. In fact, tumor cells, in particular carcinoma cells, have been shown to be enriched with sialyl $Le^x$ and sialyl $Le^a$ structures (Magnani et al., *J. Biol. Chem.* 257:14365–14369 (1982); Fukushima, supra; Kim et al., *Cancer Res.* 48:475–482 (1988) incorporated herein by reference), which are ligands for E- and P-selectins (Lowe et al., *Cell* 63:475–484 (1990); Phillips et al., *Science* 250:1130–1132 (1990); Walz et al., *Science* 250:1132–1135 (1990); Larsen et al., *Cell* 63:467–474 (1990); Berg et al., *J. Biol. Chem.* 266:14869–14972 (1991); Polley et al., *Proc. Natl. Acad. Sci. USA* 88:6224–6228 (1991) incorporated herein by reference). It has also been shown that some tumor cells aggregate with platelets (Nicolson, G. L., *Curr. Opinion Cell Biol.* 1:1009–1019 (1989) incorporated herein by reference) that presumably express E- and P-selectin. Such aggregated cells then could be trapped in capillary tubes, which could then trigger the activation of endothelial cells leading to the expression of E-selectin. It is possible that these events result in the lodging of tumor cells in capillary beds at junctions between endothelial cells (Nicolson, supra). In the case of neutrophil adhesion during inflammation, it has been shown that such E-selectins mediated adhesion leads to stronger adhesion to endothelial cells through integrins and counter receptor interaction (Springer, T. A., *Nature (Lond.)* 346:425–434 (1990) incorporated herein by reference). Once such interaction is established, neutrophils cross the boundary between endothelial cells and then establish extravasation. It was demonstrated that neutrophil extravasation can be inhibited by inhibition of the first step, rolling effect, with anti-E-selectin antibody (Lawrence et al., *Cell* 65:859–873 (1991); Ley et al., *Blood* 77:2553–2555 (1991) incorporated herein by reference). Recently, it was shown that E-selectin mediates acute lung inflammation induced by deposition of IgG immune-complexes (Mulligan et al., *J. Clin. Invest.* 88:1396–1406 (1991) incorporated herein by reference). Most recent studies demonstrated that such inflammation can be inhibited by administration of sialyl $Le^x$-glycopeptides or oligosaccharides. The present study strongly suggests that sialyl $Le^x$ positive, soluble lamp-1 can be an efficient inhibitor in such inflammatory processes. The establishment of tumor metastasis is reminiscent of this process and it is not unreasonable to assume that tumor cells may utilize the same mechanism during metastatic spread. The present invention, thus, provides means for binding selectin receptors on platelets and endothelial cells that have been activated by an immune response, thereby inhibiting or preventing binding to the selectin receptor of the native membrane-bound lamp polypeptide. The pathological conditions intended to be affected comprise, but are not limited to carcinoma cells that express sialyl $Le^x$ and/or sialyl $Le^a$ antigenic determinants, for example colon, breast, stomach, pancreatic and lung carcinoma cells. The pathological conditions intended also include leukemic cells that express sialyl $Le^x$ and/or sialyl $Le^a$ determinants as a means to escape from blood vessels into the body fluid, for example acute and chronic myelogenous leukemia cells. Other pathological conditions are those involving adhesion of circulating leukocytes to the vascular endothelium during inflammatory diseases, for example, ischemia-reperfusion injury that often occurs as a concomitant of myocardial infarction and stroke and inflammatory conditions of the lung.

Accordingly, the present invention provides soluble lamp-derived polypeptides having sialylated carbohydrate antigens that bind selectin receptors on the cell surface. The nucleic acid sequence encoding the soluble lamp-1 polypeptide is included within the sequence set forth in Table I (SEQ. ID NOS: 1,2,17,18)(from about nucleic acid number 180 to about nucleic acid number 1330). The nucleic acid sequence encoding the, soluble lamp-2 polypeptide is included within the sequence set forth in Table II (SEQ. ID NOS: 3–11, 16) (from about nucleic acid number 119 to about nucleic acid number 1568). Depending upon the cell type, purified mature lamp polypeptide has a molecular mass between 90–120 kD, whereas the soluble form has a molecular mass between 70–100 kD.

TABLE I

GAATTCGGGC GGGCTTCTTC GCTGCCGACG TACGACGAGT GGCCGGGCTC TTGCGTCTGG TAACGCGCTG TCTCTAACGC CAGCGCCGTC TCGCGCG CAC TGC 103

GCA CAG ACC ACC CGC AGA CGC CCG GCA GTC CGC AGG CCC AAA CGC GCA CGC GAC CCC GCT CTC CGC ACC GTA CCC GGC CGC CTC GGC 190

ATG GCG CCC CGC AGC GCC CGG CGA CCC CTG CTG CTG CTA CTG CCT GTT GCT GCT GCT CGG CCT CAT GCA TTG TCG TCA GCA GCC ATG 277
Met Ala Pro Arg Ser Ala Arg Arg Pro Leu Leu Leu Leu Leu Pro Val Ala Ala Ala Arg Pro His Ala Leu Ser Ser Ala Ala Met 2

TTT ATG GTG AAA AAT GGC AAC GGG ACC GCG TGC ATA ATG GCC AAC TTC TCT GCC GCC TTC TCA GTG AAC TAC GAC ACC AAG AGT GGC 364
Phe Met Val Lys Asn Gly Asn Gly Thr Ala Cys Ile Met Ala Asn Phe Ser Ala Ala Phe Ser Val Asn Tyr Asp Thr Lys Ser Gly 31

CCC AAG AAC ATG ACC TTT GAC CTG CCA TCA GAT GCC ACA GTG GTG CTC ACC CGC AGC TCC TGT GGA AAA GAG ACC ACT TCT GAC CCC 451
Pro Lys Asn Met Thr Phe Asp Leu Pro Ser Asp Ala Thr Val Val Leu Asn Arg Ser Ser Cys Gyl Lys Glu Asn Thr Ser Asp Pro 60

AGT CTC GTG ATT GCT TTT GGA AGA GGA CAT ACA CTC ACT CTC AAT TTC ACG AGA AAT GCA ACA CGT TAC AGC GTT CAG CTC ATG AGT 538
Ser Leu Val Ile Ala Phe Gly Arg Gly His Thr Leu Thr Leu Asn Phe Thr Arg Asn Ala Thr Arg Tyr Ser Val Gln Leu Met Ser 89

TTT GTT TTT AAC TTG TCA GAC ACA CAC CTT TTC CCC AAT GCG AGC TCC AAA GAA ATC AAG ACT GTG GAA TCT ATA ACT GAC ATC AGG 625
Phe Val Tyr Asn Leu Ser Asp Thr His Leu Phe Pro Asn Ala Ser Ser Lys Glu Ile Lys Thr Val Glu Ser Ile Thr Asp Ile Arg 118

GCA GAT ATA GAT AAA AAA TAC AGA TGT GTT AGT GGC ACC CAG GTC CAC ATG AAC AAC GTG ACC GTA ACG CTC CAT GAT GCC ACC ATC 712
Ala Asp Ile Asp Lys Lys Tyr Arg Cys Val Ser Gly Thr Gln Val His Met Asn Asn Val Thr Val Thr Leu His Asp Ala Thr Ile 147

CAG GCG TAC CTT TCC AAC AGC AGC TTC AGC AGG GGA GAG ACA CGC TGT GAA CAA GAC AGG CCT TCC CCA ACC ACA GCG CCC CCT GCG 799
Gln Ala Tyr Leu Ser Asn Ser Ser Phe Ser Arg Gly Glu Thr Arg Cys Glu Gln Asp Arg Pro Ser Pro Thr Thr Ala Pro Pro Ala 176

CCA CCC AGC CCC TCG CCC TCA CCC GCG CCC AAG AGC CCC TCT GTG GAC AAG TAC AAC GTG AGC GGC ACC AAC GGG ACC TGC CTG CTG 886
Pro Pro Ser Pro Ser Pro Ser Pro Val Pro Lys Ser Pro Ser Val Asp Lys Tyr Asn Val Ser Gly Thr Asn Gly Thr Cys Leu Leu 205

GCC AGC ATG GGG CTG CAG CTG AAC CTC ACC TAT GAG AGG AAG GAC AAC ACG ACG GTG ACA AGG CTT CTC AAC ATC AAC CCC AAC AAG 973
Ala Ser Met Gly Leu Gln Leu Asn Leu Thr Tyr Glu Arg Lys Asp Asn Thr Thr Val Thr Arg Leu Leu Asn Ile Asn Pro Asn Lys 234

ACC TCG GCC AGC GGG AGC TGC GGC GCC CAC CTG GTG ACT CTG GAG CTG CAC AGC GAG GGC ACC ACC GTC CTG CTC TTC CAG TTC GGG 1060
Thr Ser Ala Ser Gly Ser Cys Gly Ala His Leu Val Thr Leu Glu Leu His Ser Glu Gly Thr Thr Val Leu Leu Phe Gln Phe Gly 263

ATG AAT GCA AGT TCT AGC CGG TTT TTC CTA CAA GGA ATC CAG TTG AAT ACA ATT CTT CCT GAC GCC AGA GAC CCT GCC TTT AAA GCT 1147
Met Asn Ala Ser Ser Ser Arg Phe Phe Leu Gln Gly Ile Gln Leu Asn Thr Ile Leu Pro Asp Ala Arg Asp Pro Ala Phe Lys Ala 292

GCC AAC GGC TCC CTG CGA GCG CTG CAG GCC ACA GTC GGC AAT TCC TAC AAG TGC AAC GCG GAG GAG CAC GTC CGT GTC ACG AAG GCG 1234
Ala Asn Gly Ser Leu Arg Ala Leu Gln Ala Thr Val Gly Asn Ser Tyr Lys Cys Asn Ala Glu Glu His Val Arg Val Thr Lys Ala 321

TABLE I-continued

```
TTT TCA GTC AAT ATA TTC AAA GTG TGG GTG CAG GCT TTC AAG GTG GAA GGT GGC CAG TTT GGC TCT GTG GAG GAG TGT CTG CTG GAC 1321
Phe Ser Val Asn Ile Phe Lys Val Trp Val Gln Ala Phe Lys Val Glu Gly Gly Gln Phe Gly Ser Val Glu Glu (Cys) Leu Leu Asp 350

GAG AAC AGC ACG CTG ATC CCC ATC GCT GTG GGT GGT GCC CTG GCG GGG CTG GTC CTC ATC GTC CTC ATC GCC TAC CTC GTC GGC AGG 1408
Glu Asn Ser Thr Leu Ile Pro Ile Ala Val Gly Gly Ala Leu Ala Gly Leu Val Leu Ile Val Leu Ile Ala Tyr Leu Val Gly Arg 379
     •

AAG AGG AGT CAC GCA GGC TAC CAG ACT ATC TAG CCT GGT GCA CGC AGG CAC AGC AGC TGC AGG GGC CTC TGT TCC TTT CTC TGG GCT 1495
Lys Arg Ser His Ala Gly Tyr Gln Thr Ile end                                                                          389

TAGGGTCCTG TCGAAGGGGA GGCACACTTT CTGCAAACGT TTCTCAAATC TGCTTCATCC AATGTGAAGT TCATCTTGCA GCATTTACTA TGCACAACAG AGTAA 1600

CTATCGAAAT GACGGTGTTA ATTTTGCTAA CTGGGTTAAA TATTTTGCTA ACTGGTTAAA CATTAATATT TACCAAAGTA GGATTTTGAG GGTGGGGGTG CTCTC 1705

TCTGAGGGGG TGGGGGTGCC GCTGTCTCTG AGGGGTGGGG GTGCCGCTGT CTGAGGGGTG GGGGTGCCGC TCTCTCTGAG GGGGTGGGGG TGCCGCTTTC TCTGA 1810

GGGGGTGGGG GTGCCGCTCT CTCTGAGGGG GTGGGGGTGC TGCTCTCTCC GAGGGGTGGA ATGCCGCTGT CTCTGAGGGG TGGGGGTGCC GCTCTAAATT GGCTC 1915

CATATCATTG AGTTTAGGGT TCTGGTGTTT GGTTTCTTCA TTCTTTACTG CACTCAGATT TAAGCCTTAC AAAGGGAAAC CTCTGGCCGT CACACGTAGG ACGCA 2020

TGAAGGTCAC TCGTGTGAGG CTGACATGCT CACACATTAC AACAGTAGAG AGGGAAAATC CTAAGACAGA GGAACTCCAG AGATGAGTGT CTGGAGCGGC TTCAG 2125

TTCAGCTTTA AAGGCCAGGA CGCGCGACAC GTGGCTGGCG GCCTCGTTCC AGTGGCGGCA CGTCCTTGGC GTCTCTAATG TCTGCAGCTC AAGGGCTGGC ACTTT 2230

TTTAAATATA AAAATGGTGT TATTTTTATT TTTTTTTGTA AAGTGATTTT TGGTCTTCTG TTGACATTCG GGTGATCCTG TTCTGCGCTG TGTACAATGT GAGAT 2335

CGGTGCGTTC TCCTGATGTT TTGCCGTGGC TTGGGGATTG TACACGGGAC CAGCTCACGT AATGCATTGC CTGTAACAAT GTAATAAAAA GCCTCTTTCT TTCAA 2440

AAAAACCCCG AATTC                                                                                                  2455
```

TABLE II

CTTTTGCAAGGCTGTGGTCGGTGGTCATCAGTGCTCTTGACCCAGGTCCAGCGAGCCTTTTCCCTGGTGTTGCAGCTGTTGTTGTACCGCCGCCGTCGCCGTCGCCGCCGCCTGCTCTGCGGGGTCATGGTGTGC
Met Val Cys –25

TTCCGCCTCTTCCCGGTTCCGGGCTCAGGGCTCGTTCTGGTCTGCCTAGTCCTGG g t g a g t t g t c g g g c c c t c c c . . . >15Kb . . . a t t t t t t t a a a t g a a t c c a g GAGCTGTGCGGTCTTATGCATTGGA
Phe Arg Leu Phe Pro Val Pro Gly Ser Gly Leu Val Leu Val Leu Val Cys Leu G intron 1 ly Ala Val Arg Ser Tyr Ala Leu Gl 2

ACTTAATTTGACAGATTCAGAAAATGCCACTTGCCTTTATGCAAAATGGCAGATGAATTTCACAGTTCGCTATGAAACTACAAATAAAACTTAT g t a a g t a t a t a t t t g g g t t t . . . 1.8Kb . . . c a a a t t
uLeu Asn Leu Thr Asp Ser Glu Asn Ala Thr Cys Leu Tyr Ala Lys Trp Gln Met Asn Phe Thr Val Arg Tyr Glu Thr Thr Asn Lys Thr Tyr intron 2 33 t c t a t t t c t t t t a gAAAACTGTAACCATTTCAGACCATGGCACTGTGACATATAATGGAAGCATTTGTGGAGATGATCAGAATGGTCCCAAAATAGCAGTGCAGTTCGGACCTGGCTTTTCCTGGATTGCGAATT
Lys Thr Val Thr Ile Ser Asp His Gly Thr Val Thr Tyr Asn Gly Ser Ile Cys Gly Asp Asp Gln Asn Gly Pro Lys Ile Ala Val Gln Phe Gly Pro Gly Phe Ser Trp Ile Ala Asn P 74

TTACCAAGGCAGCATCTACTTATTCAAATGACAGCGTCTCATTTTCCTACAACACTGGTGATAACACAACATTTCCTGATGCTGAAGATAAAG g t a a c c t t a a g a a t g g a t t t . . . >3.5 kB . . . t t g t t a 105
he Thr Lys Ala Ala Ser Thr Tyr Ser Asn Asp Ser Val Ser Phe Ser Tyr Asn Thr Gly Asp Asn Thr Thr Phe Pro Asp Ala Glu Asp Lys G intron 3 a t c t t g t t t t a t a gGAATTCTTACTGTTGATGAACTTTTGGCCATCAGAATTCCATTGAATGACCTTTTTAGATGCAATAGTTTATCAACTTTGGAAAAGAATGATGTCGTCCAACACTACTGGGATGTTCTTGT
ly Ile Leu Thr Val Asp Glu Leu Leu Ala Ile Arg Ile Pro Leu Asn Asp Leu Phe Arg Cys Asn Ser Leu Ser Thr Leu Glu Lys Asn Asp Val Val Gln His Tyr Trp Asp Val Leu Va 145

ACAAGCTTTTGTCCAAAATGGCACAGTGAGCACAAATG g t g a g t a a c a a c a g a t t t t t . . . 1.1Kb . . . t c c c t t t t c g c t t g t t t t a g AGTTCCTGTGTGATAAAGACAAAACTTCAACAGTGGCACCCA
l Gln Ala Phe Val Gln Asn Gly Thr Val Ser Thr Asn G intron 4 lu Phe Leu Cys Asp Lys Asp Lys Thr Ser Thr Val Ala Pro T 172

CCATACACACCACTGTGCCATCTCCTACTACAACACCTACTCCAAAGGAAAAACCAGAACCTGGAACCTATTCAGTTAATAATGGCAATGATACTTGTCTGCGTGCTACCATGGGGCTGCAGCTGAACATCACTC
hr Ile His Thr Thr Val Pro Ser Pro Thr Thr Thr Pro Thr Pro Lys Glu Lys Pro Glu Pro Gly Thr Tyr Ser Val Asn Asn Gly Asn Asp Thr Cys Leu Leu Ala Thr Met Gly Leu Gln Leu Asn Ile Thr G 217

AGGATAAG g t a t a g g t g t c t a t c t t t a t . . . 1.8Kb . . . c c t t t c t t c t t c t c c t g a a g GTTGCTTCAGTTATTAACATCAACCCCAATACAACTCACTCCACAGGCAGCTGCCGTTCTCACACTGCTCTA
ln Asp Lys intron 5 Val Ala Ser Val Ile Asn Ile Asn Pro Asn Thr Thr His Ser Thr Gly Ser Cys Arg Ser His Thr Ala Leu 243

CTTAGACTCAATAGCAGCACCATTAAGTATCTAGACTTTGTCTTTGCTGTG g t g a g t a a c a a c a g a t t t t t . . . 3.5Kb . . . g g a a g c t c t t t t t c a a a c a g AAAAATGAAAACCGATTTTATCTGAAGGA
Leu Arg Leu Asn Ser Ser Thr Ile Lys Tyr Leu Asp Phe Val Phe Ala Val intron 6 Lys Asn Glu Asn Arg Phe Tyr Leu Lys Gl 170

AGTGAACATCAGCATGTATTTGGTTAATGGCTCCG g t a a g c a a a g c a c t g g a c c t . . . 1.2Kb . . . c c t g t t t c t t t t c t t g a a gTTTTCAGCATTGCAAATAACAATCTCAGCTACTGGGATGCCCCCCTG
uVal Asn Ile Ser Met Tyr Leu Val Asn Gly Ser V intron 7 al Phe Ser Ile Ala Asn Asn Asn Leu Ser Tyr Trp Asp Ala Pro Leu 297

GGAAGTTCTTATATGTGCAACAAAGAGCAGACTGTTTCAGTGTCTGGAGCATTTCAGATAAATACCTTTGATCTAAGGGTTCAGCCTTTCAATGTGACACAAGGAAAGTATTCTACAG g t a a g a a t c a a g c a a a c
Gly Ser Ser Tyr Met Cys Asn Lys Glu Gln Thr Val Ser Val Ser Gly Ala Phe Gln Ile Asn Thr Phe Asp Leu Arg Val Gln Pro Phe Asn Val Thr Gln Gly Lys Tyr Ser Thr A 337 t t c c . . . 18Kb . . . t g t c c t t t c t c c a c a t c t a g CTCAAGACTGCAGTGCAGATGACGACAACTTCCTTGTGCCCATAGCGGTGGGAGCTGCCTTGGCAGGAGTACTTATTCTAGTGTTGCTGGCTTATTTTATT
intron 8 la Gln Asp Cys Ser Ala Asp Asp Asp Asn Phe Leu Val Pro Ile Ala Val Gly Ala Ala Leu Ala Gly Val Leu Ile Leu Val Leu Leu Ala Tyr Phe Ile 370

GGTCTCAAGCACCATCATGCTGGATATGAGCAAATTTAGAATCTGCAACCTGATTGATTATATAAAAATACATGCAAATAACAAGATTTTCTTACCTCTCAGTTGTTGAAACACTTTGCTTCTTAAAATTGATAT
Gly Leu Lys His His His Ala Gly Tyr Glu Gln Phe * 382

GTTGAAACTTTAATTCTTTTATCAATCCCAGCATTTTGAGATCAGTCTTTATTAATAAAACCTGTTCTCTTTAATCAGCTTAAAATCCAAAGTGTCATATTTACTGGTCCTGGAGACAAACTTGTTCAAAAGAAC

ATCAACGTGCAATGTTTTAAGGGTCTATCTTAAGGAAGCCCTGGCCAAATTTTGACCTAACTTGAAGTATCCTTGAACTTATTAACATGGCCATTATAAGAATAAAATATGTAGTTGTGTCTTAATGGAATTATT

AAATGTCATTTCACTACTGGTGTTCTGTTTCAATCTATAAGGACTATAGTGATTTAAACTCATCAATGTGCCTTTGCATAAAGTTCATTAAATAAATATTGATGTGGTATAAATGCCCATCAGATATGCTTAAAC
TTGGTTTTCAGTTGAATGAAGTAGAG

As used herein, the term "purified" means that the molecule or compound is substantially free of contaminants normally associated with a native or natural environment. For example, the mature membrane-associated lamp-1 and lamp-2 polypeptides can be isolated from various methods well known to a person of skill in the art. The methods available for the purification of membrane proteins include precipitation, gel filtration, ion-exchange, reverse-phase and affinity chromatography. Other well-known methods are described in Deutscher et al., *Guide to Protein Purification: Methods in Enzymology* Vol. 182, (Academic Press 1990), which is incorporated herein by reference. Alternatively, the purified polypeptides of the present invention can also be obtained by well-known recombinant methods as described, for example in Sambrook et al., *Molecular Cloning: A Laboratory Manual* 2d ed. (Cold Spring Harbor Laboratory 1989), also incorporated herein by reference. An example of the means for preparing soluble lamp-derived polypeptide is to express nucleic acid encoding the soluble lamp in a suitable host cell, such as a bacterial, yeast or mammalian cell, using methods well known in the art, and recovering the expressed soluble protein, again using methods well known in the art. The soluble polypeptide and biologically active fragments thereof can also be produced by chemical synthesis. Synthetic polypeptides can be produced using Applied Biosystems, Inc. (Foster City, Calif.) Model 430A or 431A automatic polypeptide synthesized and chemistry provided by the manufacturer. The soluble polypeptides can also be isolated directly from cells that have been transformed with expression vectors, described below in more detail.

As used herein, "lamp-derived polypeptide" means a polypeptide having the amino acid sequence substantially the same as the amino acid sequence shown in Table I for lamp-1 or Table II for lamp-2, or active fragments thereof. As used herein the term "soluble lamp-derived polypeptide" refers to a soluble, biologically active fragment of the human lamp-1 or human lamp-2 polypeptide expressed by the extracellular domain of its respective nucleic acid. Further, "soluble polypeptide" refers to a non-naturally occurring cleaved polypeptide that functions as a secreted molecule and retains the ability to bind to the ligands recognized by its membrane counterpart, for example, cell surface selectin receptors. As used herein, an "active fragment" or "biologically active fragment" refers to any portion of the lamp polypeptide shown in Table I (SEQ ID NO: 2) or Table II (SEQ ID NO: 16) that binds to E- and/or P-selectin receptors. Methods to determine lamp binding to selectin receptors are well known to those of skill in the art, for example, as set forth below.

The invention also encompasses nucleic acid molecules which differ from that of the nucleic acid molecules shown in Table I (SEQ ID NO: 1) or Table II, (SEQ ID NOS: 3–11) but which produce the same phenotypic effect. These altered, but phenotypically equivalent nucleic acid molecules are referred to as "equivalent nucleic acids". This invention also encompasses nucleic acid molecules characterized by changes in non-coding regions that do not alter the phenotype of the polypeptides produced therefrom when compared to the nucleic acid molecule described hereinabove. This invention provides a nucleic acid molecule encoding soluble lamp-derived polypeptide wherein said nucleic acid molecule has been mutated such that the lysosomal targeting signal encoded thereby has been rendered non-functional. Methods to mutate nucleic acid molecules are well known in the art. An example of such method is site-directed mutagenesis. This invention additionally provides nucleic acid molecules which hybridize to the nucleic acid molecules of the subject invention. As used herein, the term "nucleic acid" encompasses RNA as well as single and double-stranded DNA and cDNA. As used herein, the term "polypeptide" encompasses any naturally occurring allelic variant thereof as well as recombinant forms.

This invention provides an isolated nucleic acid molecule encoding a human soluble lamp-derived polypeptide. As used herein, the term "isolated nucleic acid molecule" means a nucleic acid molecule that is in a form that does not occur in nature. Once means of isolating a human lamp-1 or human lamp-2 nucleic acid is to probe a human cDNA expression library with a natural or artificially designed antibody to human lamp-1 or human lamp-2, using methods well known in the art (see Gougos et al., *J. Biol. Chem.* 265:8361 (1990) which is incorporated herein by reference). DNA and cDNA molecules which encode human lamp polypeptides can be used to obtain complementary genomic DNA, cDNA or RNA from human or other mammalian sources.

This invention provides an antisense oligonucleotide having a sequence capable of binding specifically with any sequences of an mRNA molecule which encodes human lamp-1 or an mRNA molecule which encodes human lamp-2 so as to prevent translation of the mRNA molecule. The antisense oligonucleotide can have a sequence capable of binding specifically with any sequences of the cDNA molecule, the sequence of which is shown in Table I or Table II. As used herein, the phrase "binding specifically" encompasses the ability of a nucleic acid sequence to recognize a nucleic acid sequence complementary to its own and to form double-helical segments through hydrogen bonding between complementary base pairs. A particular example of an antisense oligonucleotide is an antisense oligonucleotide comprising chemical analogues of nucleotides.

This invention also provides a pharmaceutical composition comprising an amount of the oligonucleotide described above effective to reduce expression of a human lamp-1 or human lamp-2 polypeptide by passing through a cell membrane and binding specifically with mRNA encoding a human lamp-1 or human lamp-2 polypeptide in the cell so as to prevent its translation and a pharmaceutically acceptable hydrophobic carrier capable of passing through a cell membrane. The pharmaceutically acceptable hydrophobic carrier capable of passing through cell membranes may also comprise a structure which binds to a receptor specific for a selected cell type and is thereby taken up by cells of the selected cell type. The structure may be part of a protein known to bind to a cell-type specific receptor, for example, an insulin molecule which would target pancreatic cells. As used herein, the term "pharmaceutically acceptable carrier" encompasses any of the standard pharmaceutical carriers, such as a phosphate buffered saline solution, water and emulsions such as an oil/water or water/oil emulsion, and various types of wetting agents.

Antisense oligonucleotide drugs inhibit translation of mRNA encoding these polypeptides. Synthetic oligonucleotides, or other antisense chemical structures are designed to bind to mRNA encoding the lamp polypeptides and inhibit translation of mRNA and are useful as drugs to inhibit expression of lamp-1 and lamp-2 polypeptide genes in patients. This invention provides a means to therapeutically alter levels of expression of human lamp polypeptides by the use of a synthetic antisense oligonucleotide drug (hereinafter SAOD) which inhibits translation of mRNA encoding these polypeptides. Synthetic oligonucleotides, or other antisense chemical structures designed to recognize and selectively bind to mRNA, are constructed to be complementary to portions of the nucleotide sequences shown in Table I or Table II of DNA, RNA or chemically modified, artificial nucleic acids. The SAOD is designed to be stable in the blood stream for administration to patients by injection, or in laboratory cell culture conditions. The SAOD is designed to be capable of passing through the cell membrane in order to enter the cytoplasm of the cell by virtue of physical and chemical properties of the SAOD which render it capable of passing through cell membranes, for example, by designing small, hydrophobic SAOD chemical structures, or by virtue of specific transport systems in the cell which recognize and transport the SAOD into the cell. In addition, the SAOD can be designed for administration only to certain selected cell populations by targeting the SAOD to be recognized by specific cellular uptake mechanisms which bind and take up the SAOD only within select cell populations. For example, the SAOD may be designed to bind to a receptor found only in a certain cell type, as discussed supra. The SAOD is also designed to recognize and selectively bind to the target mRNA sequence, which may correspond to a sequence contained within the sequence shown in Table I or Table II. The SAOD is designed to inactivate the target mRNA sequence by either binding to the target mRNA and inducing degradation of the mRNA by, for example, RNase I digestion, or inhibiting translation of the mRNA target by interfering with the binding of translation-regulating factors or ribosomes, or inclusion of other chemical structures, such as ribozyme sequences or reactive chemical groups which either degrade or chemically modify the target mRNA. SAOD drugs have been shown to be capable of such properties when directed against mRNA targets (see Cohen et al., *TIPS*, 10:435 (1989) and Weintraub, *Sci. American*, January (1990), pp.40; both incorporated herein by reference). An SAOD serves as an effective therapeutic agent if it is designed to be administered in vivo or ex vivo. In this manner, an SAOD serves as a therapy to reduce lamp polypeptide expression in particular target cells of a patient, in a clinical condition which may benefit from reduced expression of lamp polypeptides, inflammatory responses and tumor cell adhesion reactions that lead to metastasis.

The invention further provides an isolated nucleic acid molecule operatively linked to a promoter of RNA transcription, as well as other regulatory sequences. As used herein, the term "operatively linked" means positioned in such a manner that the promoter will direct the transcription of RNA off of the nucleic acid molecule. Examples of such promoters are SP6, T4 and T7. Vectors which contain both a promoter and a cloning site into which an inserted nucleic acid is operatively linked to that promoter are well known in the art. Preferably, these vectors are capable of transcribing RNA in vitro or in vivo. Examples of such vectors are the pGEM series (Promega Biotech, Madison, WI).

This invention provides a vector comprising an isolated nucleic acid molecule such as DNA, cDNA or RNA encoding a soluble lamp-derived polypeptide. Examples of such vectors are viruses, such as bacteriophages, baculoviruses and retroviruses; cosmids, plasmids and other recombination vectors. Nucleic acid molecules are inserted into vector genomes by methods well known in the art. For example, insert and vector DNA can both or individually be exposed to restriction enzymes to create complementary ends on both molecules that base pair with each other and which are then joined together with a ligase. Alternatively, synthetic nucleic acid linkers can be ligated to the insert DNA that correspond to a restriction site in the vector. The vector is then digested with the respective restriction enzyme and the respective nucleic acid may then be inserted. Additionally, an oligonucleotide containing a termination codon and an appropriate restriction site can be ligated into a vector containing, for example, some or all of the following: a selectable marker gene, such as the neomycin gene for selection of stable or transient transfectants in mammalian cells; enhancer/promoter sequences from the immediate early gene of human CMV for high levels of transcription; transcription termination and RNA processing signals from SV40 for mRNA stability; SV40 polyoma origins of replication and ColE1 for proper episomal replication; versatile multiple cloning sites; and T7 and SP6 promoters for in vitro transcription of sense and anti-sense RNA. Other means are available.

Also provided are vectors comprising a DNA molecule encoding a human soluble lamp-derived polypeptide, adapted for expression in a bacterial cell, a yeast cell, a mammalian cell and other animal cells. The vectors additionally comprise the regulatory elements necessary for expression of the DNA in the bacterial, yeast, mammalian or animal cells so located relative to the DNA encoding soluble lamp-derived polypeptide as to permit expression thereof. Regulatory elements required for expression include promoter sequences to bind RNA polymerase and transcription initiation sequences for ribosome binding. For example, a bacterial expression vector includes a promoter such as the lac promoter and for transcription initiation the Shine-Dalgarno sequence and the start codon AUG (Maniatis et al., supra 1989). Similarly a eucaryotic expression vector includes a heterologous or homologous promoter for RNA polymerase II, a downstream polyadenylation signal, the start codon AUG, and a termination codon for detachment of the ribosome. Such vectors can be obtained commercially or assembled by methods well known in the art, for example, the methods described above for constructing vectors in general. Expression vectors are useful to produce cells that express the polypeptide.

This invention provides a mammalian cell containing a cDNA molecule encoding a human soluble lamp-derived polypeptide. An example is a mammalian cell comprising a plasmid adapted for expression in a mammalian cell. The plasmid has a cDNA molecule encoding a soluble lamp-derived polypeptide and the regulatory elements necessary for expression of the polypeptide. Various mammalian cells may be utilized as hosts, including, for example, mouse fibroblast cell NIH3T3, CHO cells, HeLa cells, Ltk- cells, etc. Expression plasmids such as those described supra can be used to transfect mammalian cells by methods well known in the art such as calcium phosphate precipitation, DEAE-dextran, electroporation, microinjection or lipofection.

This invention provides a pharmaceutical composition containing a pharmaceutical carrier and any of a purified, soluble polypeptide, an active fragment thereof, or a purified, mature protein and active fragments thereof, alone or in combination with each other. These polypeptides or proteins can be recombinantly derived, chemically synthesized or purified from native sources. As used herein, the term"pharmaceutically acceptable carrier" encompasses any of the standard pharmaceutical carriers, such as phosphate buffered saline solution, water and emulsions such as an oil/water or water/oil emulsion, and various types of wetting agents.

Also provided are antibodies having specific reactivity with the lamp-derived polypeptides of the subject invention. Active fragments of antibodies are encompassed within the definition of "antibody". The antibodies of the invention can be produced by any method known in the art. For example, polyclonal and monoclonal antibodies can be produced by methods well known in the art, as described, for example, in Harlow and Lane, *Antibodies: A Laboratory Manual* (Cold Spring Harbor Laboratory 1988), which is incorporated herein by reference. The polypeptide, particularly soluble lamp-derived polypeptide of the present invention, can be used as the immunogen in generating such antibodies. Altered antibodies such as chimeric, humanized, CDR-grafted or bifunctional antibodies can also be produced by methods well known in the art. Such antibodies can also be produced by hybridoma, chemical synthesis or recombinant methods described, for example, in Sambrook et al., supra, incorporated herein by reference. The antibodies can be used for determining the presence or purification of the soluble lamp-derived polypeptides of the present invention. With respect to the detection of such polypeptides, the antibodies can be used for in vitro diagnostic or in vivo imaging methods.

Immunological procedures useful for in vitro detection of the target soluble lamp-derived polypeptide in a sample include immunoassays that employ a detectable antibody. Such immunoassays include, for example, ELISA, Pandex microfluorimetric assay, agglutination assays, flow cytometry, serum diagnostic assays and immunohistochemical staining procedures which are well known in the art. An antibody can be made detectable by various means well known in the art. For example, a detectable marker can be directly or indirectly attached to the antibody. Useful markers include, for example, radionuclides, enzymes, fluorogens, chromogens and chemiluminescent labels.

This invention provides a method of modifying a biological function mediated by the regulatory activity of a selectin receptor which comprises contacting a suitable sample containing a selectin receptor with an effective amount of a biologically active lamp-derived polypeptide or a pharmaceutical composition described above. As used herein "an effective amount" refers to an amount of the polypeptide sufficient to bind to a selectin receptor and thereby prevent or inhibit its regulatory activity. This method is especially useful for modifying the regulatory activity of E-selectin or P-selectin. Examples of regulatory activities include, but are not limited to mediation of cellular adhesion to endothelial cells and platelets.

An effective amount is any amount that is effective to modify the biological function mediated by the regulatory activity of E- and/or P-selectin receptors. The method can be practiced in vitro, ex vivo or in vivo. If the method is practiced in vitro, contacting is effected by incubating the sample with a polypeptide, a protein or a pharmaceutical composition described above. The ex vivo method is similar but includes the additional step of reintroducing the treated sample into the subject.

However, in a preferred embodiment the contacting is effected in vitro by administering a polypeptide, a protein or a pharmaceutical composition, as described above to a subject, e.g., a mammal or a human.

Methods of administration are well known to those of skill in the art and include, but are not limited to, administration orally, intravenously or parenterally. Administration will be in such a dosage that the regulatory activity is effectively modified. Administration can be effected continuously or intermittently such that this amount is effective for its intended purpose.

This invention also provides a method of alleviating a pathologic condition caused by a selectin-mediated activity comprising contacting the selectin receptor with any of a purified soluble lamp-derived polypeptide, an active fragment thereof, a lamp-derived polypeptide or an active fragment thereof. The selectin receptor is bound with said polypeptide to treat the pathologic condition mediated by selectin receptor activity. As used herein "pathologic conditions" refers to any pathology arising from selectin receptor induced regulatory activity. For example, tumor cell adhesion to endothelium and leukocyte adhesion to inflammatory sites are selectin receptor mediated events.

In a preferred embodiment, the method is practiced by administering to a subject, an effective amount of a purified lamp-derived protein or a purified soluble lamp-derived polypeptide or a biologically active fragment thereof, or the pharmaceutical composition described above. Methods of administration are outlined supra.

This invention also provides a method of detecting the presence of selectin receptors on endothelial cells comprising contacting a sample of endothelial cells with a lamp-derived polypeptide, detecting binding of the lamp polypeptide to the selectin receptor, wherein said binding indicates that the endothelial cell is in an activated state (see Example IX infra).

It is understood that modifications which do not substantially affect the activity of the various molecules of this invention are also included within the definition of said molecules.

The following examples are intended to illustrate but not limit the present invention.

EXAMPLE I

Plasmid Preparation and Vector Construction

A cDNA encoding the lamp-1 molecule, designated L1-15/202 (Williams et al., *J. Cell Biol.* 111:955–966 (1990) incorporated herein by reference), was inserted into Bluescript (Stratagene, La Jolla, Calif.), resulting in pBL1-15/202. This cDNA contains the full-length coding sequence of human lamp-1 and a truncated 3'-flanking sequence. After XhoI and BamHI digestion, the cDNA insert was cloned into a pSV vector, resulting in pSVlamp-1. The pSV vector is a derivative of pJC119 (Guan et al., *Cell* 37:779–787 (1984) incorporated herein by reference). The mutant cDNA in which the cytoplasmic tyrosine is replaced with histidine was made as described (Williams et al., supra), and constructed in the same vector, resulting in pSVlamp-$1^H$.

The wild-type and mutant lamp-1 cDNAs were cloned in parallel into pcDL-SRα-478. The pcDL-SRα vector contains the SV40 promoter and the HTLV-1 LTR (Takebe et al., *Mol. Cell. Biol.* 8:466:472 (1988) incorporated herein by reference). pcDL-SRα-478 was derived from pcDL-SRα-296 to generate an EcoRI cloning site. cDNAs encoding wild-type lamp-1 and its mutant were excised from the pSV vectors described above by XhoI and BamHI and blunt-ended with the Klenow fragment of DNA polymerase I. pcDL-SRα-478 vector was digested by EcoRI, and EcoRI sites were also blunt-ended with the Klenow fragment of DNA polymerase I. Each blunt-ended cDNA was then ligated between the blunt EcoRI sites of pcDL-SRα-478. Clones containing a single lamp-1 cDNA, or mutant lamp-1 cDNA, in the proper orientation, were designated pSRαlamp-1 and pSRαlamp-$1^H$, respectively.

Plasmid pcDNA1-Fuc-TIII was constructed by first isolating from PCDM7-α(1,3/1,4)FT (Kukowska-Latallo et al. *Genes Develop.* 4:1288–1303 (1990); Weston et al. *J. Biol. Chem.* 267:24575–24584 (1992) incorporated herein by reference) a 2.2 kb XhoI fragment corresponding to the Fuc-TIII cDNA. This fragment was then cloned into the sense orientation into the unique XhoI site in plasmid pcDNAI (Invitrogen, San Diego, Calif.).

EXAMPLE II

Amplification of E-selectin Sequences

Human E-selection cDNA sequence was amplified by polymerase chain reaction (PCR) (Higuchi et al., *Nucl. Acids Res.* 16:7351–7367 (1988) incorporated herein by reference) using a human endothelial cDNA library (Staunton et al., *Cell* 52:925–933 (1988) incorporated herein by reference) as a template. The cDNA library was constructed from mRNA of activated human endothelial cells (Staunton et al., supra). The 5'-,primer sequence was 5'-TCAAGTACTCTTGAAGTCATGATTGCTTCA-3' (SEQ ID NO: 12) and corresponds to -9 to +12 nucleotides with respect to the translation initiation codon with a ScaI restriction site at the 5'-end. The 3'-primer sequence was 5'-TGAAGTACTAACTTAAAGGATGTAAGAAGGCTT-3' (SEQ ID NO 13). This sequence corresponds in anti-sense to -18 to +6 bp with respect to the stop codon with the ScaI restriction site at the 5' end. Amplification of cDNA was achieved after 40 cycles under the following conditions: denaturation for 1 minute at 94° C., annealing for 2 minutes at 55° C., and polymerization for 3 minutes at 72° C. The amplified DNA was cut with ScaI and cloned into the EcoRV site of Bluescript/ks. The cDNA insert was then excised by digestion with ScaI and KpnI. pcDL-SRα-478 was first digested with EcoRI and the EcoRI site was blunt-ended by the Klenow fragment of DNA polymerase I. The blunt-ended plasmid was then digested with KpnI, which is situated 3' to the EcoRI site. The SmaI-KpnI fragment representing the E-selectin cDNA was cloned between the blunt EcoRI-KpnI ends of pcDL-SRα-478 to yield pSRα-E-selectin.

EXAMPLE III

Amplification of Lamp Sequences

A cDNA encoding soluble lamp-1 was amplified by PCR using the pSV lamp-1 as a template. The 5'-primer sequence was 5'-TTTGAATTCCTCGCGCCATGGCGCC-3' (SEQ ID NO: 14). This corresponds to −8 to +8 bp relative to the initiation codon plus an EcoRI restriction site and TTT at 5'-end. The 3'-primer sequence is 5'-AAAGGTACCTAGCTGTTCTCGTCCAGCAG-3' (SEQ ID NO: 15. This sequence contains the lamp-1 sequence in anti-sense from codons 348 to 353, after which a stop codon is introduced. The sequence also contains AAA plus a KpnI site. After amplification under the same conditions described above, the DNA was cut with EcoRI and KpnI and then cloned into the EcoRI/KpnI sites of pcDL-SRα-478, to yield pSRαs-lamp-1.

EXAMPLE IV

Establishment of SP Colonic Cells Expressing Various Amounts of Lamp-1 on the Cell Surface The isolation and characterization of the poorly metastatic human colon carcinoma line KM12-SP (hereinafter SP) has been previously described (Saitoh et al., supra; Morikawa et al., *Cancer Res.* 48:1943–1948 (1988) incorporated herein by reference). This cell line expresses less lamp-1 on the cell surface than its highly metastatic counterpart, L4 (Saitoh et al., supra). SP colonic cells are poorly metastatic in nude mouse experiments and express only 3% of the total lamp-1 on the cell surface (Saitoh et al., supra).

In order to establish SP cells that express an increased amount of cell surface lamp-1, SP colonic cells were transfected with vectors that express wild-type, membrane-tethered lamp-1 (pSVlamp-1 and pSRαlamp-1). The cells were co-transfected with $pSV_2neo$. The ratio of plasmids harboring lamp-1 cDNAs and $pSV_2neo$ was 10:1. After transfection, the cells were selected with G418 (1 mg/ml), in DME containing 10% fetal calf serum, sodium pyruvate, MEM vitamin solution, non-essential amino acids, and antibiotics. After culturing for 10 days in the presence of G418, clonal cell lines were obtained by limiting dilution and different clones were examined by immunofluorescence for cell surface expression of lamp-1.

Similarly, in a second set of experiments, increased lamp-1 cell surface expression was sought by expressing a mutant lamp-1 in which a cytoplasmic tyrosine residue critical for lysosomal targeting (Williams et al., supra) had been changed to a histidine residue (vectors pSVlamp-$1^H$ and pSRαlamp-$1^H$). The resulting mutant lamp-1 molecule, in contrast to its wild-type counterpart, does not sort to the lysosome, and therefore accumulates preferentially at the cell surface via its default biosynthetic pathway.

Several SP cell lines were derived from transfections with each of the four lamp-1 vectors. FIG. 1 illustrates a flow cytometry analysis of cell surface lamp-1 expression in representative clones containing these different vectors. These cell lines each express roughly at least two-fold more cell surface lamp-1 (mean fluorescent intensities ~20, ~35, ~40, ~60) than does the parental SP cell line (mean fluorescent intensity=~13). Cells transfected with pSRαlamp-1 express more cell surface lamp-1 (FIG. 1B, mean fluorescence intensity=~35) than do cells transfected with pSVlamp-1 (FIG. 1A, mean fluorescent intensity=~20), and cells expressing the mutant lamp-1 express more surface-localized lamp-1 than do cells expressing the wild-type lamp-1 (FIG. 1, compare panels C and D, mean fluorescence intensities=~40 and ~60, respectively, versus panel A and B, respective mean fluorescence intensities of ~20 and ~35).

EXAMPLE V

Establishment of CHO Cell Lines Expressing E-Selectin

CHO cells were co-transfected with pSRαE-selectin and $pSV_2dhfr$ in a 10:1 molar ratio, using the lipofectin procedure. After the transfection, cells were cultured in α-MEM without nucleotides for 14 days. The cells were then propagated with increasing concentration of methotrexate (Sigma, St. Louis, Mo.) final concentration of 0.5 μM and cloned cell lines were obtained in 24-well tissue culture plates. Each clone was tested for HL-60 cell binding as a screen for cell surface E-selectin expression. Clones that efficiently bound HL-60 cells were subsequently tested by immunofluorescence using an anti-E-selectin antibody to confirm E-selectin expression.

EXAMPLE VI

Expression of Soluble Lamp-1 in CHO Cells

In order to produce a soluble lamp-1 molecule that displays sialyl $Le^x$ determinants, CHO cells were first co-transfected by the lipofectin procedure (Bierhuizen et al., *Proc. Natl. Acad. Sci. USA* 84:9326–9330 (1992) incorporated herein by reference) with pcDNA1-Fuc-TIII and pHyg (Sugden et al., *Molec. Cell. Biol.* 5:410–413 (1985) incorporated herein by reference) in a 10:1 molar ratio. The transfected cells were selected in the presence of 500 μg/ml of hygromycin (Sigma, St. Louis, Mo.) and the cloned in a 24-well tissue culture plate. Each cell line was assessed for the expression of sialyl $Le^x$ by immunofluorescence. Immunofluorescence staining was carried out using a mouse monoclonal anti-sialyl $Le^x$ antibody, CSLEX (Fukushima et al., supra) (purchased from UCLA tissue culture laboratory), followed by staining with rhodamine-conjugated goat anti-mouse IgM, using procedures described previously (Williams et al., supra).

A clonal cell line stably expressing sialyl $Le^x$ molecules was then co-transfected with pSRα s-lamp-1 and $pSV_2dhfr$, and the transfected cells were selected in α-MEM without nucleotides. After culturing under these conditions for 14 days, the cells were propagated for gene amplification by methotrexate as described above. Expression of soluble lamp-1 was determined by immunoblotting of the conditioned medium. The conditioned medium from each well was concentrated (Centricon 30, Amicon Inc., Beverly, Mass.), and the concentrated medium was applied to a nitrocellulose membrane. After blocking with 5% milk in PBS, the membrane was incubated at room temperature for 1 hour with rabbit anti-lamp-1 antibody diluted in 20 mM Tris-HCl, pH 7.5 containing 1% BSA and 0.5M NaCl (buffer A). The membrane was then washed for 5 minutes at room temperature with 20 mM Tris-HCl, pH 7.5 containing 0.5M NaCl and 0.05% Tween-20 twice and with the same buffer without Tween-20, and then incubated with alkaline phosphatase-conjugated goat anti-rabbit antibody in buffer A. The blot was then washed with the same buffer, and incubated with alkaline phosphatase substrate (5-bromo-4-chloro-3-indolylphosphate and nitroblue tetrazolium in 10 mM Tris-HCl, 2 mM $MgCl_2$, pH 9.0) using procedures previously described (Blake et al., *Anal. Biochem.* 136:175–179 (1984) incorporated herein by reference). One cell line that produced an abundant amount of soluble lamp-1, as determined with this procedure, was chosen for further study.

EXAMPLE VII

Purification of Soluble Lamp-1 from the Conditioned Medium of CHO Cells

The CHO cell line expressing soluble lamp-1 was cultured in α-MEM containing 0.5 μM methotrexate, and the medium was replaced with Opti-MEM (BRL, Bethesda, Md.) after the cells reached confluency. After culturing for 3 days, the conditioned medium (260 ml) was collected and applied to a column (1.2×2.5 cm) of wheat germ agglutinin-Agarose (E-Y Laboratories, San Mateo, Calif.). The column was equilibrated with 10 mM potassium phosphate buffer, pH 7.4 containing 0.14M NaCl and eluted with 100 mM GlcNAc in the same buffer. The eluate was dialyzed against 50 mM potassium phosphate buffer, pH 7.0, containing 1 mM EDTA and the sample was applied to a column (2 ml) of DEAE-Sephadex (Sigma, St. Louis, Mo.) equilibrated with the same buffer. The column was eluted with the same buffer containing 0.1M NaCl without EDTA. The eluted sample was then dialyzed against PBS, and tested in adhesion assays.

EXAMPLE VIII

Flow Cytometry Analysis

SP cells expressing various amounts of cell surface lamp-1 were stained with the mouse IgG anti-human-lamp-1 antibody, BB6 (Carlsson et al., *J. Biol. Chem.* 264(34):20526–20531 (1989) incorporated herein by reference); ascites diluted 1:500. Cells were then stained with fluorescein-conjugated goat anti-mouse IgG (40 μg/ml) (Sigma, St. Louis Mo.) and subjected to analysis by flow cytometry on a FACScan (Becton Dickinson, Mountain View, Calif.). Cell staining was measured in arbitrary units as the log of fluorescent intensity and displayed on a four decade scale.

EXAMPLE IX

Colonic Carcinoma Cells Adhere to IL-1β Treated Endothelia Through E-selectin Binding to Sialyl $Le^x$ Structures The four lamp-1 transfected SP cell lines (SP-pSVlamp-1, SP-pSRαlamp-1, SP-pSVlamp-$1^H$, or SP-pSRαlamp-$1^H$), and the control SP cell line were then subjected to adhesion assays to determine their relative abilities to exhibit E-selectin-dependent adhesive properties.

Adhesion of SP cells to human umbilical vein endothelial cells, hereinafter HUVEC, (Clonetics, San Diego, Calif.) was carried out as described previously (Phillips et al., supra) with a slight modification. Briefly, SP cells were metabolically labeled with [$^{35}$S]-methionine (100 μCi/ml, ICN) in methionine-free DME for 2 hours as described previously (Lee et al., *J. Biol. Chem.* 265:20476–20487 (1990) incorporated herein by reference). The [$^{35}$S]-methionine labeled SP cells were harvested in the cell dissociation solution (Specialty Media, Lavellette, N.J.) and washed twice with DME before assay of the binding to HUVEC. HUVEC monolayers cultured in 96-well tissue culture plates, were activated with 5 unit/ml of IL-1β (Boehringer-Mannheim, Indianapolis, Ind.) for 4 hours and then washed with DME containing 5% fetal calf serum. Control non-activated HUVEC monolayers were prepared identically (without Il-1β), and used in parallel for adhesion assays.

Approximately $1\times10^5$ of $^{35}$S-labeled SP cells were added to the HUVEC monolayers in 0.1 ml of DME containing 5% fetal calf serum. After incubation at 37° C. for 15 minutes, the cells were washed with the same solution three times. Adherent cells remaining after washing were dissolved in 0.1 ml of cell dissolution solution. The solution containing the solubilized cells was added to 2 ml of Aquamix scintillation cocktail, and radioactivity was determined by scintillation counting. The amount of radioactivity in the cells added to each well was determined independently, and was used to determine the fraction of applied cells that actually adhered to the monolayers in each microliter well. In order to test the inhibitory activity of soluble lamp-1, purified soluble lamp-1 was dialyzed against PBS and aliquots, serially diluted in DME containing 5% fetal calf serum, were added to microtiter wells containing activated HUVEC monolayers. After incubation for 15 minutes at 4° C., the monolayers were used in adhesion assays as described above.

Figure 2B:
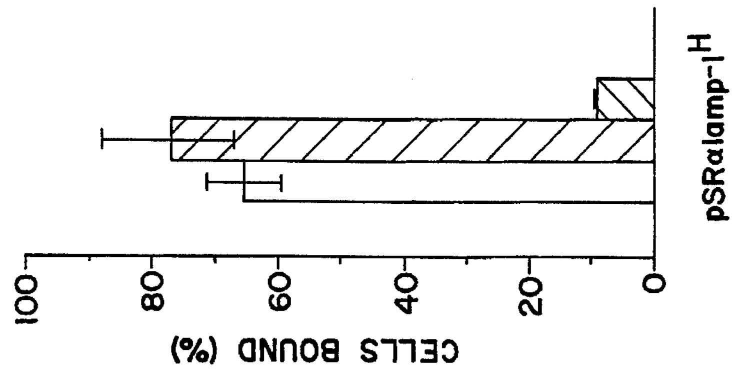
FIG. 2B shows the inhibition of adhesion to endothelial cells by sialyl $Le^x$ glycolipid. The SP cell line transfected with the pSRαlamp-$1^H$ vector was subjected to adhesion to activated HUVEC monolayers exactly as in panel A (open bar), or as in panel A after pre-treatment of the activated monolayers with liposomes containing sialyl Lewis$^x$ glycolipid (hatched bar), or after pre-treatment with liposomes containing the control glycolipid paragloboside (cross-hatched bars). Data correspond to the fraction of applied cells still adherent after washing, and are the mean and one standard deviation, from four replicate assays.
Figure 2A:
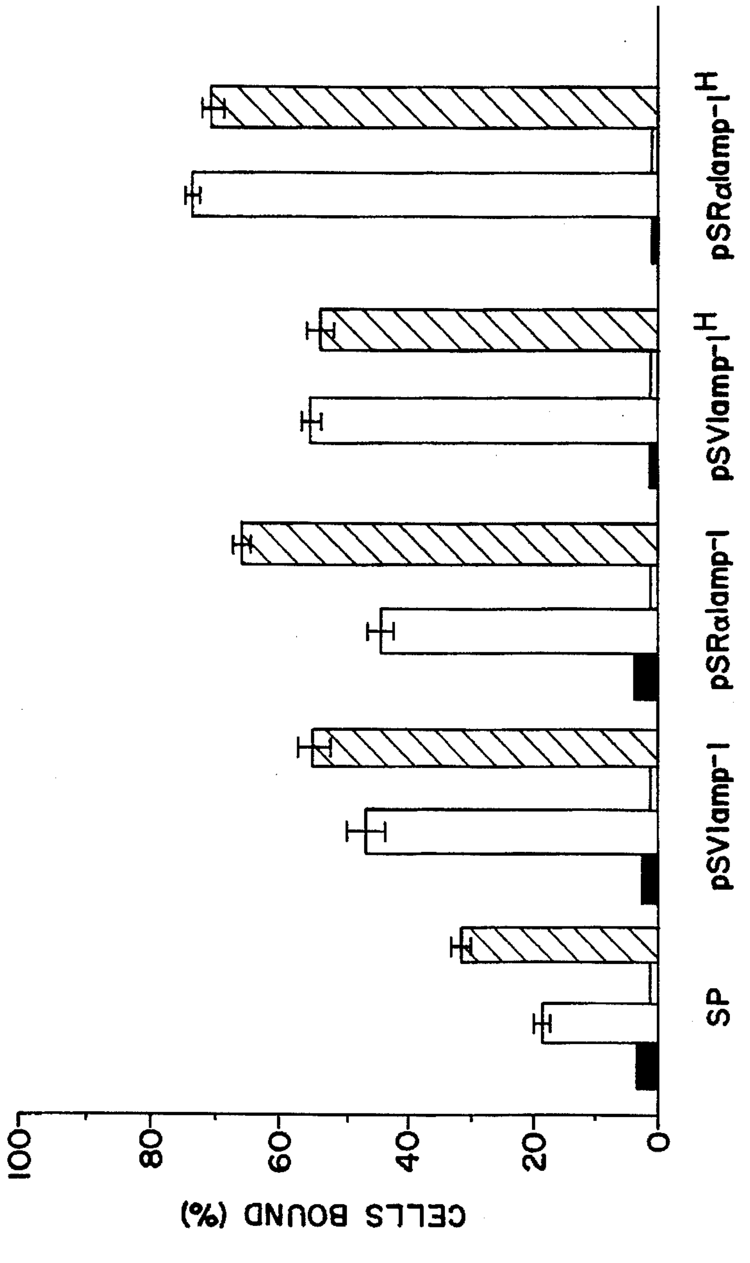
FIG. 2A shows adhesion of various SP colonic carcinoma cells to endothelial cells or E-selectin expressing CHO cells. SP cells transfected with lamp-1 expression vectors (pSVlamp-1, pSRαlamp-1, pSVlamp-$1^H$, or pSRαlamp-$1^H$), or the parental SP cells were used in adhesion assays as described in the Examples. Adhesion to IL-1β-activated HUVEC monolayers is indicated by the open bars, whereas adhesion to non-activated HUVECS is represented by the solid bars. Adhesion to E-selectin-expressing CHO cell monolayers is denoted by the hatched bars, and the cross-hatched bars depict adhesion to control CHO cell monolayers. Data shown correspond to the fraction of applied cells that remained after washing, and represent the mean and standard deviation derived from four replicate assays.

A substantial fraction of cells expressing recombinant cell surface lamp-1 bound to HUVEC monolayers, which were induced to express E-selectin by pre-treatment with IL1-β, whereas the same cells did not bind detectably to non-activated HUVECS (FIG. 2A). The parental SP cells bound only modestly to activated HUVEC monolayers. Essentially all of the adhesion observed with the lamp-1 transfected cell lines is E-selectin-dependent, since binding of the cell line expressing the largest amount of cell surface lamp-1

(transfected with pSRαlamp-$1^H$, see FIG. 1) may be virtually completely blocked by pre-treatment of the monolayers with liposomes containing sialyl $Lewis^x$ glycolipid (FIG. 2B). Under the same conditions, control liposomes did not have an effect.

Binding of SP cells to CHO cells expressing E-selectin was carried out in the same way except that the activation by IL-1β was omitted. Inhibition by sialyl $Le^x$ glycolipid (Kameyama et al. *Carbohydr. Res.* 209:C1–C4 (1991) incorporated herein by reference), NeuNAcα2→3Galβ1→4 (Fucα1→3)GlcNAcβ1→3Galβ1→4Glc-Cer was tested exactly as described (Phillips et al., supra). Paragloboside, NeuNAcα2→3Galβ1→4GlcNAcβ1→3Galβ1→4Glc-Cer was used as a control glycolipid.

Similar results were obtained in experiments using CHO cells expressing E-selectin. Again, cells expressing increased levels of cell surface lamp-1 bound to E-selectin-expressing CHO monolayers, but not to control CHO monolayers that do not express E-selectin (FIG. 2A). The control, parent SP cells bound moderately to the CHO cell monolayer expressing E-selectin. When considered with the data shown in FIG. 1, these observations indicate that the ability to exhibit E-selectin-dependent adhesion in this static adhesion assay may be conferred upon the SP cells by affecting only a modest increase in cell surface lamp-1 expression. The two-fold increase in cell surface lamp-1 expression shown by pSVlamp-1-transfected cells, relative to the control SP cells (FIG. 1, compare SP vs pSVlamp-1) appears sufficient to enable the SP cells to efficiently adhere to E-selectin. Moreover, increased adhesion is seen when higher levels of cell surface lamp-1 are present. (for example, compare binding and lamp-1 expression of pSVlamp-1 transfectants; 48% bound, mean fluorescent intensity of ~20, versus binding and lamp-1 expression of pSRαlamp-$1^H$ transfectants; ~75% bound, mean fluorescent intensity of ~60). These results establish that the lamp-1 on the cell surface carry ligands for E-selectin, and the degree of binding is roughly proportional to the amount of lamp-1 expressed on the cell surface.

EXAMPLE X

Comparison of Cell Surface Sialyl $Le^x$ Expression Among SP Cells Expressing Different Amounts of Cell Surface Lamp-1

Cell surface lamp-1 molecules are heavily substituted with N- and O-linked oligosaccharide molecules that can terminate in the sialyl $Lewis^x$ moiety (Lee et al., supra), an essential component of the oligosaccharide ligand for E-selectin. It therefore seemed possible that increased lamp-1 expression in turn would yield a concomitant increase in cell surface sialyl $Lewis^x$ moieties (displayed by surface localized lamp-1 molecules), and that this would confer E-selectin-dependent adhesion competence upon the lamp-1 transfectants.

Figure 3:
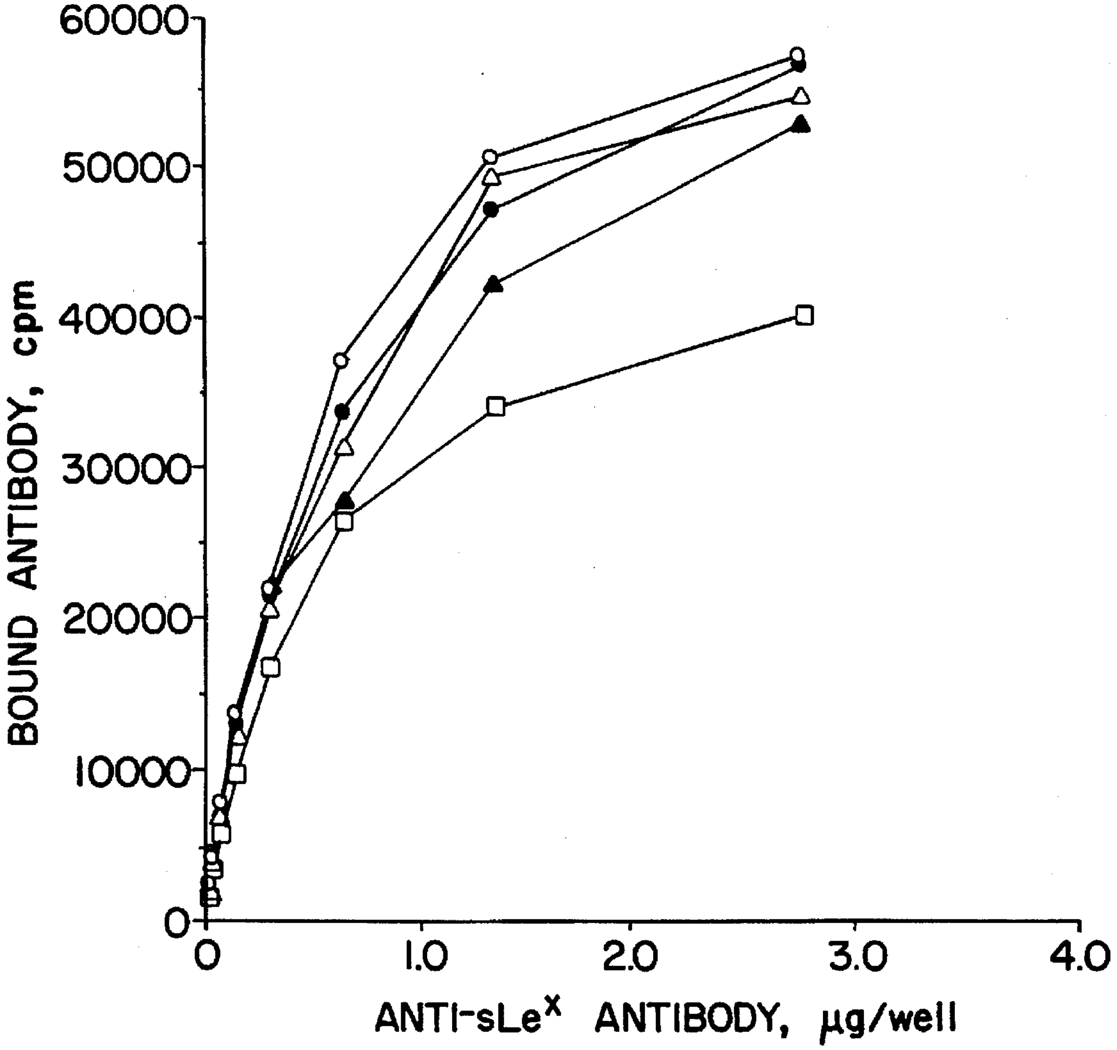
FIG. 3 shows binding of anti-sialyl $Le^x$ antibody to various SP-cells. Increasing concentrations of monoclonal antibody specific to sialyl $Le^x$ were incubated with cells, and binding was determined as described in the "Examples." Cells tested are SP cells transfected with pSVlamp-1 (▲), pSRαlamp-1 (Δ), pSVαlamp-1$^H$ (●), pSRαlamp-1$^H$ (○), and the parental SP cells (□). All of the transfected cells are the same as shown in FIG. 1.

A radioactive antibody binding assay was used to quantitate cell surface sialyl $Lewis^x$ termini on the cell lines that express recombinant lamp-1, and on the parental SP cells. The number of binding sites for the monoclonal anti-sialyl $Le^x$ antibody was measured as detailed previously (Saitoh et al., supra). At near-saturating levels of anti-sialyl $Lewis^x$ antibody, each of the cell lines that expresses supra-control level of lamp-1 also displayed a substantially higher level of cell surface sialyl $Lewis^x$ immunoreactivity than the level displayed by the control SP cells (FIG. 3). These data are most consistent with the hypothesis that the level of cell surface lamp-1 expression can directly determine cell surface sialyl $Lewis^x$ expression levels, and thus also E-selectin-dependent cell adhesion.

EXAMPLE XI

Soluble Lamp-1 Can Inhibit E-Selectin Mediated Binding

The data obtained from the experiments detailed above support an essential role for lamp-1 in mediating E-selectin-dependent cell adhesion of tumor cells, by functioning to present sialyl $Lewis^x$ to E-selectin in a manner analogous to that proposed for L-selectin on leukocytes (Picker et al., *Cell* 66:921–933 (1991) incorporated herein by reference). It also suggests that soluble lamp-1 molecules that display sialyl $Lewis^x$-terminated oligosaccharides may effectively disrupt E-selectin-dependent cell adhesion by displacing cell-associated sialyl $Lewis^x$ binding site(s) on E-selectin.

Figure 4A:
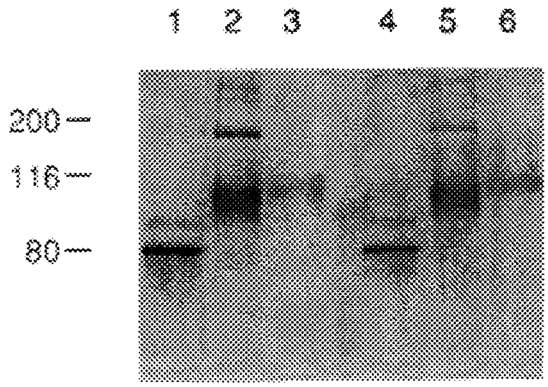
FIGS. 4A and 4B show the purification of soluble lamp-1 generated from control CHO cells and CHO cells expressing sialyl $Le^x$ structures. The culture medium from the CHO cells (lanes 1,4) are successively applied to wheat germ agglutinin columns (lanes 2,5) and DEAE-Sephadex column (lanes 3,6). Lanes 1–3 are the samples isolated from the control CHO cells while lanes 4–6 are the samples isolated from the CHO cells expressing sialyl $Le^x$ structures.
Figure 4B:
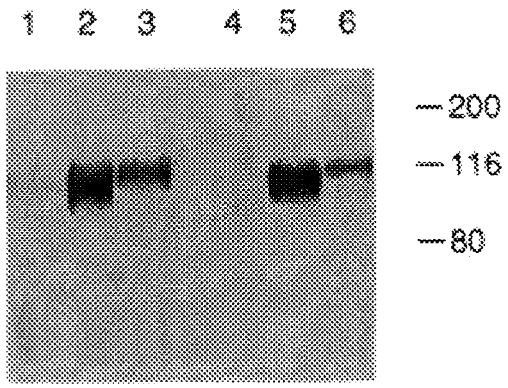

A soluble lamp-1 molecule that displays the sialyl $Lewis^x$ moiety was prepared and its ability to block E-selectin-dependent adhesion of lamp-1-expressing SP cells was tested. This reagent was prepared from CHO cells stably transfected with a vector that directs the expression of a soluble form of lamp-1, and with a vector that encodes a human α(1,3)fucosyltransferase (Fuc-TIII) (Kukowska-Latallo et al., supra) capable of creating the sialyl $Lewis^x$ determinant using endogenous CHO cell oligosaccharide precursors (Lowe et al., supra). The transfected cells were confirmed to express sialyl $Le^x$ determinants by immunofluorescence as described (Williams et al., supra). This recombinant molecule was purified from media collected from these cells using wheat germ agglutinin and DEAE-Sephadex column chromatography procedures. The product of this purification consisted largely of a single polypeptide (FIG. 4A) which by Western blotting reacted with anti-lamp-1 antibodies (FIG. 4B).

A soluble lamp-1 molecule lacking the sialyl $Lewis^x$ determinant was purified in an identical manner, using a control CHO cell line stably transfected only with the vector that synthesizes soluble lamp-1 molecules. This purified control protein also reacts with anti-lamp-1 (FIG. 4B).

Figure 5:
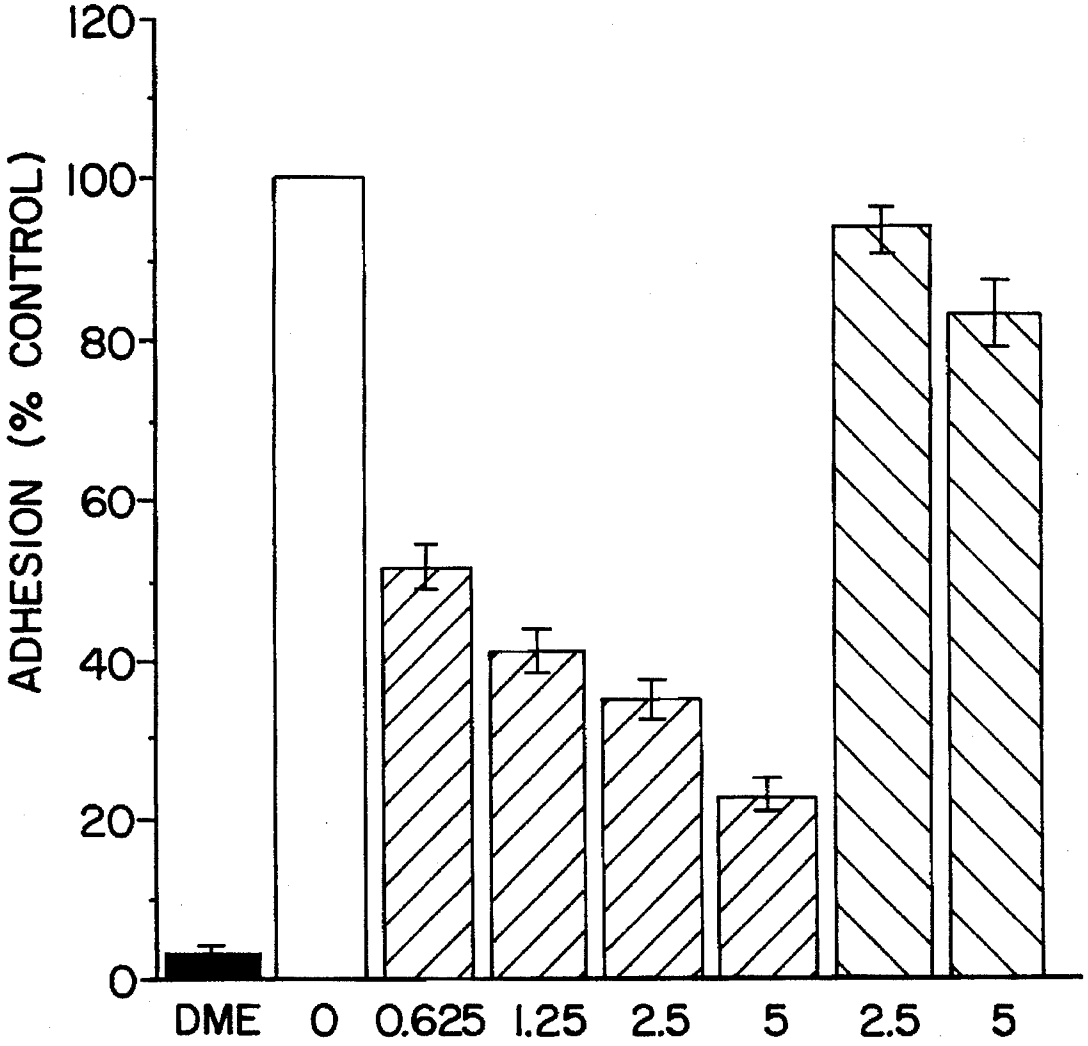
FIG. 5 shows the inhibition of cell adhesion to HUVEC by soluble lamp-1. The adhesion of SP cells transfected with pSRαlamp-1$^H$, the same as shown in FIG. 1, was tested for inhibition by soluble lamp-1 derived from sialyl $Le^x$ positive CHO cells (hatched bars). The control soluble lamp-1 was obtained from control CHO cells that do not express sialyl $Le^x$ (cross-hatched bars). The amount of soluble lamp-1 is expressed as μg/50 μl. The open bar represents the control without the inhibitors while the closed bar represents the adhesion to unstimulated HUVEC monolayers. One standard deviation is indicated at the top of each bar.

Using the adhesion assay previously shown to be E-selectin-dependent (FIG. 2B), it was determined that the concentration-dependent inhibition of adhesion of pSRαlamp-1-transfected SP cells to activated HUVEC monolayers (FIG. 5). By contrast, the control, sialyl $Lewis^x$-negative lamp-1 molecule inhibited the binding minimally, even at a concentration that for the sialyl $Lewis^x$-positive protein diminished binding to 20% of control levels. These results indicate that the sialyl $Lewis^x$ determinant achieves a conformation on the soluble lamp-1 glycoprotein that is recognized by E-selectin with an affinity sufficient to compete with the cell surface sialyl $Lewis^x$ determinants that mediate adhesion to this selectin. These results further suggest that this reagent, and analogous ones, may prove useful as therapeutic agents which block selectin-dependent inflammation or tumor metastasis.

Although the invention has been described with reference to the disclosed embodiments, it should be understood that various modifications can be made without departing from the spirit of the invention. Accordingly, the invention is limited only by the following claims.

SEQUENCE LISTING ( 1 ) GENERAL INFORMATION:

( i i i ) NUMBER OF SEQUENCES: 18

( 2 ) INFORMATION FOR SEQ ID NO:1:

( i ) SEQUENCE CHARACTERISTICS:
( A ) LENGTH: 2455 base pairs
( B ) TYPE: nucleic acid
( C ) STRANDEDNESS: double
( D ) TOPOLOGY: linear ( i x ) FEATURE:
( A ) NAME/KEY: CDS
( B ) LOCATION: 191..1438

( x i ) SEQUENCE DESCRIPTION: SEQ ID NO:1:

GAATTCGGGC GGGCTTCTTC GCTGCCGACG TACGACGAGT GGCCGGGCTC TTGCGTCTGG 60

TAACGCGCTG TCTCTAACGC CAGCGCCGTC TCGCGCGCAC TGCGCACAGA CCACCCGCAG 120

ACGCCCGGCA GTCCGCAGGC CCAAACGCGC ACGCGACCCC GCTCTCCGCA CCGTACCCGG 180

CCGCCTCGGC ATG GCG CCC CGC AGC GCC CGG CGA CCC CTG CTG CTG CTA 229
Met Ala Pro Arg Ser Ala Arg Arg Pro Leu Leu Leu Leu
1 5 10

CTG CCT GTT GCT GCT GCT CGG CCT CAT GCA TTG TCG TCA GCA GCC ATG 277
Leu Pro Val Ala Ala Ala Arg Pro His Ala Leu Ser Ser Ala Ala Met
15 20 25

TTT ATG GTG AAA AAT GGC AAC GGG ACC GCG TGC ATA ATG GCC AAC TTC 325
Phe Met Val Lys Asn Gly Asn Gly Thr Ala Cys Ile Met Ala Asn Phe
30 35 40 45

TCT GCT GCC TTC TCA GTG AAC TAC GAC ACC AAG AGT GGC CCC AAG AAC 373
Ser Ala Ala Phe Ser Val Asn Tyr Asp Thr Lys Ser Gly Pro Lys Asn
50 55 60

ATG ACC TTT GAC CTG CCA TCA GAT GCC ACA GTG GTG CTC AAC CGC AGC 421
Met Thr Phe Asp Leu Pro Ser Asp Ala Thr Val Val Leu Asn Arg Ser
65 70 75

TCC TGT GGA AAA GAG AAC ACT TCT GAC CCC AGT CTC GTG ATT GCT TTT 469
Ser Cys Gly Lys Glu Asn Thr Ser Asp Pro Ser Leu Val Ile Ala Phe
80 85 90

GGA AGA GGA CAT ACA CTC ACT CTC AAT TTC ACG AGA AAT GCA ACA CGT 517
Gly Arg Gly His Thr Leu Thr Leu Asn Phe Thr Arg Asn Ala Thr Arg
95 100 105

TAC AGC GTT CAG CTC ATG AGT TTT GTT TAT AAC TTG TCA GAC ACA CAC 565
Tyr Ser Val Gln Leu Met Ser Phe Val Tyr Asn Leu Ser Asp Thr His
110 115 120 125

CTT TTC CCC AAT GCG AGC TCC AAA GAA ATC AAG ACT GTG GAA TCT ATA 613
Leu Phe Pro Asn Ala Ser Ser Lys Glu Ile Lys Thr Val Glu Ser Ile
130 135 140

ACT GAC ATC AGG GCA GAT ATA GAT AAA AAA TAC AGA TGT GTT AGT GGC 661
Thr Asp Ile Arg Ala Asp Ile Asp Lys Lys Tyr Arg Cys Val Ser Gly
145 150 155

ACC CAG GTC CAC ATG AAC AAC GTG ACC GTA ACG CTC CAT GAT GCC ACC 709
Thr Gln Val His Met Asn Asn Val Thr Val Thr Leu His Asp Ala Thr
160 165 170

ATC CAG GCG TAC CTT TCC AAC AGC AGC TTC AGC AGG GGA GAG ACA CGC 757
Ile Gln Ala Tyr Leu Ser Asn Ser Ser Phe Ser Arg Gly Glu Thr Arg
175 180 185

TGT GAA CAA GAC AGG CCT TCC CCA ACC ACA GCG CCC CCT GCG CCA CCC 805
Cys Glu Gln Asp Arg Pro Ser Pro Thr Thr Ala Pro Pro Ala Pro Pro
190 195 200 205

-continued

```
AGC CCC TCG CCC TCA CCC GTG CCC AAG AGC CCC TCT GTG GAC AAG TAC   853
Ser Pro Ser Pro Ser Pro Val Pro Lys Ser Pro Ser Val Asp Lys Tyr
                210                 215                 220

AAC GTG AGC GGC ACC AAC GGG ACC TGC CTG CTG GCC AGC ATG GGG CTG   901
Asn Val Ser Gly Thr Asn Gly Thr Cys Leu Leu Ala Ser Met Gly Leu
            225                 230                 235

CAG CTG AAC CTC ACC TAT GAG AGG AAG GAC AAC ACG ACG GTG ACA AGG   949
Gln Leu Asn Leu Thr Tyr Glu Arg Lys Asp Asn Thr Thr Val Thr Arg
        240                 245                 250

CTT CTC AAC ATC AAC CCC AAC AAG ACC TCG GCC AGC GGG AGC TGC GGC   997
Leu Leu Asn Ile Asn Pro Asn Lys Thr Ser Ala Ser Gly Ser Cys Gly
    255                 260                 265

GCC CAC CTG GTG ACT CTG GAG CTG CAC AGC GAG GGC ACC ACC GTC CTG  1045
Ala His Leu Val Thr Leu Glu Leu His Ser Glu Gly Thr Thr Val Leu
270                 275                 280                 285

CTC TTC CAG TTC GGG ATG AAT GCA AGT TCT AGC CGG TTT TTC CTA CAA  1093
Leu Phe Gln Phe Gly Met Asn Ala Ser Ser Ser Arg Phe Phe Leu Gln
                290                 295                 300

GGA ATC CAG TTG AAT ACA ATT CTT CCT GAC GCC AGA GAC CCT GCC TTT  1141
Gly Ile Gln Leu Asn Thr Ile Leu Pro Asp Ala Arg Asp Pro Ala Phe
            305                 310                 315

AAA GCT GCC AAC GGC TCC CTG CGA GCG CTG CAG GCC ACA GTC GGC AAT  1189
Lys Ala Ala Asn Gly Ser Leu Arg Ala Leu Gln Ala Thr Val Gly Asn
        320                 325                 330

TCC TAC AAG TGC AAC GCG GAG GAG CAC GTC CGT GTC ACG AAG GCG TTT  1237
Ser Tyr Lys Cys Asn Ala Glu Glu His Val Arg Val Thr Lys Ala Phe
    335                 340                 345

TCA GTC AAT ATA TTC AAA GTG TGG GTC CAG GCT TTC AAG GTG GAA GGT  1285
Ser Val Asn Ile Phe Lys Val Trp Val Gln Ala Phe Lys Val Glu Gly
350                 355                 360                 365

GGC CAG TTT GGC TCT GTG GAG GAG TGT CTG CTG GAC GAG AAC AGC ACG  1333
Gly Gln Phe Gly Ser Val Glu Glu Cys Leu Leu Asp Glu Asn Ser Thr
                370                 375                 380

CTG ATC CCC ATC GCT GTG GGT GGT GCC CTG GCG GGG CTG GTC CTC ATC  1381
Leu Ile Pro Ile Ala Val Gly Gly Ala Leu Ala Gly Leu Val Leu Ile
            385                 390                 395

GTC CTC ATC GCC TAC CTC GTC GGC AGG AAG AGG AGT CAC GCA GGC TAC  1429
Val Leu Ile Ala Tyr Leu Val Gly Arg Lys Arg Ser His Ala Gly Tyr
        400                 405                 410

CAG ACT ATC TAGCCTGGTG CACGCAGGCA CAGCAGCTGC AGGGGCCTCT          1478
Gln Thr Ile
    415

GTTCCTTTCT CTGGGCTTAG GGTCCTGTCG AAGGGGAGGC ACACTTTCTG CAAACGTTTC  1538

TCAAATCTGC TTCATCCAAT GTGAAGTTCA TCTTGCAGCA TTTACTATGC ACAACAGAGT  1598

AACTATCGAA ATGACGGTGT TAATTTTGCT AACTGGGTTA AATATTTTGC TAACTGGTTA  1658

AACATTAATA TTTACCAAAG TAGGATTTTG AGGGTGGGGG TGCTCTCTCT GAGGGGGTGG  1718

GGGTGCCGCT GTCTCTGAGG GGTGGGGGTG CCGCTGTCTG AGGGGTGGGG GTGCCGCTCT  1778

CTCTGAGGGG GTGGGGGTGC CGCTTTCTCT GAGGGGGTGG GGGTGCCGCT CTCTCTGAGG  1838

GGGTGGGGGT GCTGCTCTCT CCGAGGGGTG GAATGCCGCT GTCTCTGAGG GGTGGGGGTG  1898

CCGCTCTAAA TTGGCTCCAT ATCATTGAGT TTAGGGTTCT GGTGTTTGGT TTCTTCATTC  1958

TTTACTGCAC TCAGATTTAA GCCTTACAAA GGGAAACCTC TGGCCGTCAC ACGTAGGACG  2018

CATGAAGGTC ACTCGTGTGA GGCTGACATG CTCACACATT ACAACAGTAG AGAGGGAAAA  2078

TCCTAAGACA GAGGAACTCC AGAGATGAGT GTCTGGAGCG GCTTCAGTTC AGCTTTAAAG  2138

GCCAGGACGC GCGACACGTG GCTGGCGGCC TCGTTCCAGT GGCGGCACGT CCTTGGCGTC  2198
```

-continued

```
TCTAATGTCT GCAGCTCAAG GGCTGGCACT TTTTTAAATA TAAAAATGGT GTTATTTTTA   2258

TTTTTTTTTG TAAAGTGATT TTTGGTCTTC TGTTGACATT CGGGTGATCC TGTTCTGCGC   2318

TGTGTACAAT GTGAGATCGG TGCGTTCTCC TGATGTTTTG CCGTGGCTTG GGGATTGTAC   2378

ACGGGACCAG CTCACGTAAT GCATTGCCTG TAACAATGTA ATAAAAAGCC TCTTTCTTTC   2438

AAAAAAACCC CGAATTC                                                  2455
```

( 2 ) INFORMATION FOR SEQ ID NO:2:

( i ) SEQUENCE CHARACTERISTICS:
( A ) LENGTH: 416 amino acids
( B ) TYPE: amino acid
( D ) TOPOLOGY: linear ( i i ) MOLECULE TYPE: protein ( x i ) SEQUENCE DESCRIPTION: SEQ ID NO:2:

```
Met Ala Pro Arg Ser Ala Arg Arg Pro Leu Leu Leu Leu Leu Pro Val
  1             5                  10                  15

Ala Ala Ala Arg Pro His Ala Leu Ser Ser Ala Ala Met Phe Met Val
             20                  25                  30

Lys Asn Gly Asn Gly Thr Ala Cys Ile Met Ala Asn Phe Ser Ala Ala
         35                  40                  45

Phe Ser Val Asn Tyr Asp Thr Lys Ser Gly Pro Lys Asn Met Thr Phe
     50                  55                  60

Asp Leu Pro Ser Asp Ala Thr Val Val Leu Asn Arg Ser Ser Cys Gly
 65                  70                  75                  80

Lys Glu Asn Thr Ser Asp Pro Ser Leu Val Ile Ala Phe Gly Arg Gly
                 85                  90                  95

His Thr Leu Thr Leu Asn Phe Thr Arg Asn Ala Thr Arg Tyr Ser Val
            100                 105                 110

Gln Leu Met Ser Phe Val Tyr Asn Leu Ser Asp Thr His Leu Phe Pro
        115                 120                 125

Asn Ala Ser Ser Lys Glu Ile Lys Thr Val Glu Ser Ile Thr Asp Ile
    130                 135                 140

Arg Ala Asp Ile Asp Lys Lys Tyr Arg Cys Val Ser Gly Thr Gln Val
145                 150                 155                 160

His Met Asn Asn Val Thr Val Thr Leu His Asp Ala Thr Ile Gln Ala
                165                 170                 175

Tyr Leu Ser Asn Ser Ser Phe Ser Arg Gly Glu Thr Arg Cys Glu Gln
            180                 185                 190

Asp Arg Pro Ser Pro Thr Thr Ala Pro Pro Ala Pro Pro Ser Pro Ser
        195                 200                 205

Pro Ser Pro Val Pro Lys Ser Pro Ser Val Asp Lys Tyr Asn Val Ser
    210                 215                 220

Gly Thr Asn Gly Thr Cys Leu Leu Ala Ser Met Gly Leu Gln Leu Asn
225                 230                 235                 240

Leu Thr Tyr Glu Arg Lys Asp Asn Thr Thr Val Thr Arg Leu Leu Asn
                245                 250                 255

Ile Asn Pro Asn Lys Thr Ser Ala Ser Gly Ser Cys Gly Ala His Leu
            260                 265                 270

Val Thr Leu Glu Leu His Ser Glu Gly Thr Thr Val Leu Leu Phe Gln
        275                 280                 285

Phe Gly Met Asn Ala Ser Ser Ser Arg Phe Phe Leu Gln Gly Ile Gln
    290                 295                 300

Leu Asn Thr Ile Leu Pro Asp Ala Arg Asp Pro Ala Phe Lys Ala Ala
```

-continued

```
305                           310                           315                           320

Asn Gly Ser Leu Arg Ala Leu Gln Ala Thr Val Gly Asn Ser Tyr Lys
                325                 330                 335

Cys Asn Ala Glu Glu His Val Arg Val Thr Lys Ala Phe Ser Val Asn
            340                 345                 350

Ile Phe Lys Val Trp Val Gln Ala Phe Lys Val Glu Gly Gly Gln Phe
        355                 360                 365

Gly Ser Val Glu Glu Cys Leu Leu Asp Glu Asn Ser Thr Leu Ile Pro
    370                 375                 380

Ile Ala Val Gly Gly Ala Leu Ala Gly Leu Val Leu Ile Val Leu Ile
385                 390                 395                 400

Ala Tyr Leu Val Gly Arg Lys Arg Ser His Ala Gly Tyr Gln Thr Ile
                405                 410                 415
```

( 2 ) INFORMATION FOR SEQ ID NO:3:

( i ) SEQUENCE CHARACTERISTICS:
( A ) LENGTH: 210 base pairs
( B ) TYPE: nucleic acid
( C ) STRANDEDNESS: double
( D ) TOPOLOGY: linear ( x i ) SEQUENCE DESCRIPTION: SEQ ID NO:3:

```
CTTTTGCAAG GCTGTGGTCG GTGGTCATCA GTGCTCTTGA CCCAGGTCCA GCGAGCCTTT    60
TCCCTGGTGT TGCAGCTGTT GTTGTACCGC CGCCGTCGCC GCCGTCGCCG CCTGCTCTGC   120
GGGGTCATGG TGTGCTTCCG CCTCTTCCCG GTTCCGGGCT CAGGGCTCGT TCTGGTCTGC   180
CTAGTCCTGG GTGAGTTGTC GGGCCCTCCC                                    210
```

( 2 ) INFORMATION FOR SEQ ID NO:4:

( i ) SEQUENCE CHARACTERISTICS:
( A ) LENGTH: 159 base pairs
( B ) TYPE: nucleic acid
( C ) STRANDEDNESS: double
( D ) TOPOLOGY: linear ( x i ) SEQUENCE DESCRIPTION: SEQ ID NO:4:

```
ATTTTTTTAA ATGAATCCAG GAGCTGTGCG GTCTTATGCA TTGGAACTTA ATTTGACAGA    60
TTCAGAAAAT GCCACTTGCC TTTATGCAAA ATGGCAGATG AATTTCACAG TTCGCTATGA   120
AACTACAAAT AAAACTTATG TAAGTATATA TTTGGGTTT                          159
```

( 2 ) INFORMATION FOR SEQ ID NO:5:

( i ) SEQUENCE CHARACTERISTICS:
( A ) LENGTH: 254 base pairs
( B ) TYPE: nucleic acid
( C ) STRANDEDNESS: double
( D ) TOPOLOGY: linear ( x i ) SEQUENCE DESCRIPTION: SEQ ID NO:5:

```
CAAATTTCTA TTTCTTTTAG AAAACTGTAA CCATTTCAGA CCATGGCACT GTGACATATA    60
ATGGAAGCAT TTGTGGGGAT GATCAGAATG GTCCCAAAAT AGCAGTGCAG TTCGGACCTG   120
GCTTTTCCTG GATTGCGAAT TTTACCAAGG CAGCATCTAC TTATTCAAAT GACAGCGTCT   180
CATTTTCCTA CAACACTGGT GATAACACAA CATTTCCTGA TGCTGAAGAT AAAGGTAACC   240
TTAAGAATGG ATTT                                                     254
```

( 2 ) INFORMATION FOR SEQ ID NO:6:

-continued ( i ) SEQUENCE CHARACTERISTICS:
( A ) LENGTH: 199 base pairs
( B ) TYPE: nucleic acid
( C ) STRANDEDNESS: double
( D ) TOPOLOGY: linear ( x i ) SEQUENCE DESCRIPTION: SEQ ID NO:6:

TTGTTAATCT TGTTTTATAG GAATTCTTAC TGTTGATGAA CTTTTGGCCA TCAGAATTCC 60

ATTGAATGAC CTTTTTAGAT GCAATAGTTT ATCAACTTTG GAAAAGAATG ATGTTGTCCA 120

ACACTACTGG GATGTTCTTG TACAAGCTTT TGTCCAAAAT GGCACAGTGA GCACAAATGG 180

TGAGTAACAA CAGATTTTT 199

( 2 ) INFORMATION FOR SEQ ID NO:7:

( i ) SEQUENCE CHARACTERISTICS:
( A ) LENGTH: 225 base pairs
( B ) TYPE: nucleic acid
( C ) STRANDEDNESS: double
( D ) TOPOLOGY: linear ( x i ) SEQUENCE DESCRIPTION: SEQ ID NO:7:

TCCCTTTTCG CTTGTTTTAG AGTTCCTGTG TGATAAAGAC AAAACTTCAA CAGTGGCACC 60

CACCATACAC ACCACTGTGC CATCTCCTAC TACAACACCT ACTCCAAAGG AAAAACCAGA 120

ACCTGGAACC TATTCAGTTA ATAATGGCAA TGATACTTGT CTGCGTGCTA CCATGGGGCT 180

GCAGCTGAAC ATCACTCAGG ATAAGGTATA GGTGTCTATC TTTAT 225

( 2 ) INFORMATION FOR SEQ ID NO:8:

( i ) SEQUENCE CHARACTERISTICS:
( A ) LENGTH: 163 base pairs
( B ) TYPE: nucleic acid
( C ) STRANDEDNESS: double
( D ) TOPOLOGY: linear ( x i ) SEQUENCE DESCRIPTION: SEQ ID NO:8:

CCTTTCTTCT TCTCCTGAAG GTTGCTTCAG TTATTAACAT CAACCCCAAT ACAACTCACT 60

CCACAGGCAG CTGCCGTTCT CACACTGCTC TACTTAGACT CAATAGCAGC ACCATTAAGT 120

ATCTAGACTT TGTCTTTGCT GTGGTGAGTA ACAACAGATT TTT 163

( 2 ) INFORMATION FOR SEQ ID NO:9:

( i ) SEQUENCE CHARACTERISTICS:
( A ) LENGTH: 104 base pairs
( B ) TYPE: nucleic acid
( C ) STRANDEDNESS: double
( D ) TOPOLOGY: linear ( x i ) SEQUENCE DESCRIPTION: SEQ ID NO:9:

GGAAGCTCTT TTTCAAACAG AAAAATGAAA ACCGATTTTA TCTGAAGGAA GTGAACATCA 60

GCATGTATTT GGTTAATGGC TCCGGTAAGC AAAGCACTGG ACCT 104

( 2 ) INFORMATION FOR SEQ ID NO:10:

( i ) SEQUENCE CHARACTERISTICS:
( A ) LENGTH: 205 base pairs
( B ) TYPE: nucleic acid
( C ) STRANDEDNESS: double
( D ) TOPOLOGY: linear ( x i ) SEQUENCE DESCRIPTION: SEQ ID NO:10:

CCTGTTTCTT TTCTTTGAAG TTTTCAGCAT TGCAAATAAC AATCTCAGCT ACTGGGATGC 60

-continued

CCCCCTGGGA AGTTCTTATA TGTGCAACAA AGAGCAGACT GTTTCAGTGT CTGGAGCATT 120

TCAGATAAAT ACCTTTGATC TAAGGGTTCA GCCTTTCAAT GTGACACAAG GAAAGTATTC 180

TACAGGTAAG AATCAAGCAA ACTTC 205

( 2 ) INFORMATION FOR SEQ ID NO:11:

( i ) SEQUENCE CHARACTERISTICS:
( A ) LENGTH: 687 base pairs
( B ) TYPE: nucleic acid
( C ) STRANDEDNESS: double
( D ) TOPOLOGY: linear ( x i ) SEQUENCE DESCRIPTION: SEQ ID NO:11:

TGTCCTTTCT CCACATCTAG CTCAAGACTG CAGTGCAGAT GACGACAACT TCCTTGTGCC 60

CATAGCGGTG GGAGCTGCCT TGGCAGGAGT ACTTATTCTA GTGTTGCTGG CTTATTTTAT 120

TGGTCTCAAG CACCATCATG CTGGATATGA GCAATTTTAG AATCTGCAAC CTGATTGATT 180

ATATAAAAAT ACATGCAAAT AACAAGATTT TCTTACCTCT CAGTTGTTGA AACACTTTGC 240

TTCTTAAAAT TGATATGTTG AAACTTTAAT TCTTTTATCA ATCCCAGCAT TTTGAGATCA 300

GTCTTTATTA ATAAAACCTG TTCTCTTTAA TCAGCTTAAA ATCCAAAGTG TCATATTTAC 360

TGGTCCTGGA GACAAACTTG TTCAAAAGAA CATCAACGTG CAATGTTTTA AGGGTCTATC 420

TTAAGGAAGC CCTGGCCAAA TTTTGACCTA ACTTGAAGTA TCCTTGAACT TATTAACATG 480

GCCATTATAA GAATAAAATA TGTAGTTGTG TCTTAATGGA ATTAATAAAT GTCATTTCAC 540

TACTGGTGTT CTGTTTCAAT CTATAAGGAC TATAGTGATT TAAACTCATC AATGTGCCTT 600

TGCATAAAGT TCATTAAATA AATATTGATG TGGTATAAAT GCCCATCAGA TATGCTTAAA 660

CTTGGTTTTC AGTTGAATGA AGTAGAG 687

( 2 ) INFORMATION FOR SEQ ID NO:12:

( i ) SEQUENCE CHARACTERISTICS:
( A ) LENGTH: 30 base pairs
( B ) TYPE: nucleic acid
( C ) STRANDEDNESS: single
( D ) TOPOLOGY: linear ( x i ) SEQUENCE DESCRIPTION: SEQ ID NO:12:

TCAAGTACTC TTGAAGTCAT GATTGCTTCA 30

( 2 ) INFORMATION FOR SEQ ID NO:13:

( i ) SEQUENCE CHARACTERISTICS:
( A ) LENGTH: 33 base pairs
( B ) TYPE: nucleic acid
( C ) STRANDEDNESS: single
( D ) TOPOLOGY: linear ( x i ) SEQUENCE DESCRIPTION: SEQ ID NO:13:

TGAAGTACTA ACTTAAAGGA TGTAAGAAGG CTT 33

( 2 ) INFORMATION FOR SEQ ID NO:14:

( i ) SEQUENCE CHARACTERISTICS:
( A ) LENGTH: 25 base pairs
( B ) TYPE: nucleic acid
( C ) STRANDEDNESS: single
( D ) TOPOLOGY: linear ( x i ) SEQUENCE DESCRIPTION: SEQ ID NO:14:

TTTGAATTCC TCGCGCCATG GCGCC 25

( 2 ) INFORMATION FOR SEQ ID NO:15:

( i ) SEQUENCE CHARACTERISTICS:
( A ) LENGTH: 29 base pairs
( B ) TYPE: nucleic acid
( C ) STRANDEDNESS: single
( D ) TOPOLOGY: linear ( x i ) SEQUENCE DESCRIPTION: SEQ ID NO:15:

AAAGGTACCT AGCTGTTCTC GTCCAGCAG 29

( 2 ) INFORMATION FOR SEQ ID NO:16:

( i ) SEQUENCE CHARACTERISTICS:
( A ) LENGTH: 410 amino acids
( B ) TYPE: amino acid
( D ) TOPOLOGY: linear ( x i ) SEQUENCE DESCRIPTION: SEQ ID NO:16:

Met Val Cys Phe Arg Leu Phe Pro Val Pro Gly Ser Gly Leu Val Leu
1 5 10 15

Val Leu Val Cys Leu Gly Ala Val Arg Ser Tyr Ala Leu Glu Leu Asn
20 25 30

Leu Thr Asp Ser Glu Asn Ala Thr Cys Leu Tyr Ala Lys Trp Gln Met
35 40 45

Asn Phe Thr Val Arg Tyr Glu Thr Thr Asn Lys Thr Tyr Lys Thr Val
50 55 60

Thr Ile Ser Asp His Gly Thr Val Thr Tyr Asn Gly Ser Ile Cys Gly
65 70 75 80

Asp Asp Gln Asp Gly Pro Lys Ile Ala Val Gln Phe Gly Pro Gly Phe
85 90 95

Ser Trp Ile Ala Asn Phe Thr Lys Ala Ala Ser Thr Tyr Ser Asn Asp
100 105 110

Ser Val Ser Phe Ser Tyr Asn Thr Gly Asp Asn Thr Thr Phe Pro Asp
115 120 125

Ala Glu Asp Lys Gly Ile Leu Thr Val Asp Glu Leu Leu Ala Ile Arg
130 135 140

Ile Pro Leu Asn Asp Leu Phe Arg Cys Asn Ser Leu Ser Thr Leu Glu
145 150 155 160

Lys Asn Asp Val Val Gln His Tyr Trp Asp Val Leu Val Gln Ala Phe
165 170 175

Val Gln Asn Gly Thr Val Ser Thr Asn Glu Phe Leu Cys Asp Lys Asp
180 185 190

Lys Thr Ser Thr Val Ala Pro Thr Ile His Thr Thr Val Pro Ser Pro
195 200 205

Thr Thr Thr Pro Thr Pro Lys Glu Lys Pro Glu Pro Gly Thr Tyr Ser
210 215 220

Val Asn Asn Gly Asn Asp Thr Cys Leu Leu Ala Thr Met Gly Leu Gln
225 230 235 240

Leu Asn Ile Thr Gln Asp Lys Val Ala Ser Val Ile Asn Ile Asn Pro
245 250 255

Asn Thr Thr His Ser Thr Gly Ser Cys Arg Ser His Thr Ala Leu Leu
260 265 270

Arg Leu Asn Ser Ser Thr Ile Lys Tyr Leu Asp Phe Val Phe Ala Val
275 280 285

Lys Asn Glu Asn Arg Phe Tyr Leu Lys Glu Val Asn Ile Ser Met Tyr
290 295 300

-continued

Leu Val Asn Gly Ser Val Phe Ser Ile Ala Asn Asn Asn Leu Ser Tyr
305 310 315 320

Trp Asp Ala Pro Leu Gly Ser Ser Tyr Met Cys Asn Lys Glu Gln Thr
325 330 335

Val Ser Val Ser Gly Ala Phe Gln Ile Asn Thr Phe Asp Leu Arg Val
340 345 350

Gln Pro Phe Asn Val Thr Gln Gly Lys Tyr Ser Thr Ala Gln Asp Cys
355 360 365

Ser Ala Asp Asp Asp Asn Phe Leu Val Pro Ile Ala Val Gly Ala Ala
370 375 380

Leu Ala Gly Val Leu Ile Leu Val Leu Leu Ala Tyr Phe Ile Gly Leu
385 390 395 400

Lys His His His Ala Gly Tyr Glu Gln Phe
405 410

( 2 ) INFORMATION FOR SEQ ID NO:17:

( i ) SEQUENCE CHARACTERISTICS:
( A ) LENGTH: 353 amino acids
( B ) TYPE: amino acid
( D ) TOPOLOGY: linear ( x i ) SEQUENCE DESCRIPTION: SEQ ID NO:17:

Ala Met Phe Met Val Lys Asn Gly Asn Gly Thr Ala Cys Ile Met Ala
1 5 10 15

Asn Phe Ser Ala Ala Phe Ser Val Asn Tyr Asp Thr Lys Ser Gly Pro
20 25 30

Lys Asn Met Thr Phe Asp Leu Pro Ser Asp Ala Thr Val Val Leu Asn
35 40 45

Arg Ser Ser Cys Gly Lys Glu Asn Thr Ser Asp Pro Ser Leu Val Ile
50 55 60

Ala Phe Gly Arg Gly His Thr Leu Thr Leu Asn Phe Thr Arg Asn Ala
65 70 75 80

Thr Arg Tyr Ser Val Gln Leu Met Ser Phe Val Tyr Asn Leu Ser Asp
85 90 95

Thr His Leu Phe Pro Asn Ala Ser Ser Lys Glu Ile Lys Thr Val Glu
100 105 110

Ser Ile Thr Asp Ile Arg Ala Asp Ile Asp Lys Lys Tyr Arg Cys Val
115 120 125

Ser Gly Thr Gln Val His Met Asn Asn Val Thr Val Thr Leu His Asp
130 135 140

Ala Thr Ile Gln Ala Tyr Leu Ser Asn Ser Ser Phe Ser Arg Gly Glu
145 150 155 160

Thr Arg Cys Glu Gln Asp Arg Pro Ser Pro Thr Thr Ala Pro Pro Ala
165 170 175

Pro Pro Ser Pro Ser Pro Ser Pro Val Pro Lys Ser Pro Ser Val Asp
180 185 190

Lys Tyr Asn Val Ser Gly Thr Asn Gly Thr Cys Leu Leu Ala Ser Met
195 200 205

Gly Leu Gln Leu Asn Leu Thr Tyr Glu Arg Lys Asp Asn Thr Thr Val
210 215 220

Thr Arg Leu Leu Asn Ile Asn Pro Asn Lys Thr Ser Ala Ser Gly Ser
225 230 235 240

Cys Gly Ala His Leu Val Thr Leu Glu Leu His Ser Glu Gly Thr Thr
245 250 255

Val Leu Leu Phe Gln Phe Gly Met Asn Ala Ser Ser Ser Arg Phe Phe

-continued 260 265 270

Leu Gln Gly Ile Gln Leu Asn Thr Ile Leu Pro Asp Ala Arg Asp Pro
275 280 285

Ala Phe Lys Ala Ala Asn Gly Ser Leu Arg Ala Leu Gln Ala Thr Val
290 295 300

Gly Asn Ser Tyr Lys Cys Asn Ala Glu Glu His Val Arg Val Thr Lys
305 310 315 320

Ala Phe Ser Val Asn Ile Phe Lys Val Trp Val Gln Ala Phe Lys Val
325 330 335

Glu Gly Gly Gln Phe Gly Ser Val Glu Glu Cys Leu Leu Asp Glu Asn
340 345 350

Ser ( 2 ) INFORMATION FOR SEQ ID NO:18:

( i ) SEQUENCE CHARACTERISTICS:
( A ) LENGTH: 380 amino acids
( B ) TYPE: amino acid
( D ) TOPOLOGY: linear ( x i ) SEQUENCE DESCRIPTION: SEQ ID NO:18:

Met Ala Pro Arg Ser Ala Arg Arg Pro Leu Leu Leu Leu Leu Pro Val
1 5 10 15

Ala Ala Ala Arg Pro His Ala Leu Ser Ser Ala Ala Met Phe Met Val
20 25 30

Lys Asn Gly Asn Gly Thr Ala Cys Ile Met Ala Asn Phe Ser Ala Ala
35 40 45

Phe Ser Val Asn Tyr Asp Thr Lys Ser Gly Pro Lys Asn Met Thr Phe
50 55 60

Asp Leu Pro Ser Asp Ala Thr Val Val Leu Asn Arg Ser Ser Cys Gly
65 70 75 80

Lys Glu Asn Thr Ser Asp Pro Ser Leu Val Ile Ala Phe Gly Arg Gly
85 90 95

His Thr Leu Thr Leu Asn Phe Thr Arg Asn Ala Thr Arg Tyr Ser Val
100 105 110

Gln Leu Met Ser Phe Val Tyr Asn Leu Ser Asp Thr His Leu Phe Pro
115 120 125

Asn Ala Ser Ser Lys Glu Ile Lys Thr Val Glu Ser Ile Thr Asp Ile
130 135 140

Arg Ala Asp Ile Asp Lys Lys Tyr Arg Cys Val Ser Gly Thr Gln Val
145 150 155 160

His Met Asn Asn Val Thr Val Thr Leu His Asp Ala Thr Ile Gln Ala
165 170 175

Tyr Leu Ser Asn Ser Ser Phe Ser Arg Gly Glu Thr Arg Cys Glu Gln
180 185 190

Asp Arg Pro Ser Pro Thr Thr Ala Pro Pro Ala Pro Pro Ser Pro Ser
195 200 205

Pro Ser Pro Val Pro Lys Ser Pro Ser Val Asp Lys Tyr Asn Val Ser
210 215 220

Gly Thr Asn Gly Thr Cys Leu Leu Ala Ser Met Gly Leu Gln Leu Asn
225 230 235 240

Leu Thr Tyr Glu Arg Lys Asp Asn Thr Thr Val Thr Arg Leu Leu Asn
245 250 255

Ile Asn Pro Asn Lys Thr Ser Ala Ser Gly Ser Cys Gly Ala His Leu
260 265 270

-continued

| | | | | | | | | | | | | | | | |
|---|---|---|---|---|---|---|---|---|---|---|---|---|---|---|---|
| Val | Thr | Leu<br>275 | Glu | Leu | His | Ser | Glu<br>280 | Gly | Thr | Thr | Val | Leu<br>285 | Leu | Phe | Gln |
| Phe | Gly<br>290 | Met | Asn | Ala | Ser | Ser<br>295 | Ser | Arg | Phe | Phe | Leu<br>300 | Gln | Gly | Ile | Gln |
| Leu<br>305 | Asn | Thr | Ile | Leu | Pro<br>310 | Asp | Ala | Arg | Asp | Pro<br>315 | Ala | Phe | Lys | Ala | Ala<br>320 |
| Asn | Gly | Ser | Leu | Arg<br>325 | Ala | Leu | Gln | Ala | Thr<br>330 | Val | Gly | Asn | Ser | Tyr<br>335 | Lys |
| Cys | Asn | Ala | Glu<br>340 | Glu | His | Val | Arg | Val<br>345 | Thr | Lys | Ala | Phe | Ser<br>350 | Val | Asn |
| Ile | Phe | Lys<br>355 | Val | Trp | Val | Gln | Ala<br>360 | Phe | Lys | Val | Glu | Gly<br>365 | Gly | Gln | Phe |
| Gly | Ser<br>370 | Val | Glu | Glu | Cys | Leu<br>375 | Leu | Asp | Glu | Asn | Ser<br>380 | | | | |

What is claimed:

1. A lamp-1 polypeptide having the amino acid sequence shown in SEQ ID NO.: 17, wherein the lamp-1 polypeptide is glycosylated with sialyl $Le^x$, soluble in an aqueous solvent and binds to E-selectin.

2. The lamp-1 polypeptide of claim 1 produced by a method comprising the steps of:

a. inserting into a suitable vector a nucleic acid molecule encoding the lamp-1 polypeptide of claim 1;

b. transfecting the resulting vector into a suitable host cell that expresses fucosyltransferase enzyme;

c. culturing the resulting host cell under conditions suitable for the expression of the lamp-1 polypeptide; and d. recovering the lamp-1 polypeptide so produced.

3. A pharmaceutical composition comprising a pharmaceutically acceptable carrier and the lamp-1 polypeptide of claim 1.

4. A lamp-1 polypeptide having the amino acid sequence shown in SEQ ID NO.: 18, wherein the lamp-1 polypeptide is glycosylated with sialyl $Le^x$, soluble in an aqueous solvent and binds to E-selectin.

5. The lamp-1 polypeptide of claim 4 produced by the method comprising:

a. inserting into a suitable vector a nucleic acid molecule encoding the lamp-1 polypeptide of claim 4;

b. transfecting the resulting vector into a suitable host cell that expresses fucosyltransferase enzyme;

c. culturing the resulting host cell under conditions suitable for the expression of the lamp-1 polypeptide; and d. recovering the lamp-1 polypeptide so produced.

6. A pharmaceutical composition comprising a pharmaceutically acceptable carrier and the lamp-1 polypeptide of claim 4.

* * * * *